(12) United States Patent
Kawahara et al.

(10) Patent No.: US 10,323,354 B2
(45) Date of Patent: Jun. 18, 2019

(54) FINE CELLULOSE FIBER SHEET

(71) Applicant: Asahi Kasei Fibers Corporation, Osaka-shi, Osaka (JP)

(72) Inventors: Kazufumi Kawahara, Tokyo (JP); Daisuke Sato, Tokyo (JP); Hirofumi Ono, Tokyo (JP); Yamato Saito, Tokyo (JP)

(73) Assignee: Asahi Kasei Fibers Corporation, Osaka (JP)

( * ) Notice: Subject to any disclaimer, the term of this patent is extended or adjusted under 35 U.S.C. 154(b) by 251 days.

(21) Appl. No.: 14/905,215

(22) PCT Filed: Jul. 18, 2014

(86) PCT No.: PCT/JP2014/069248
§ 371 (c)(1),
(2) Date: Jan. 14, 2016

(87) PCT Pub. No.: WO2015/008868
PCT Pub. Date: Jan. 22, 2015

(65) Prior Publication Data
US 2016/0177512 A1    Jun. 23, 2016

(30) Foreign Application Priority Data

Jul. 19, 2013   (JP) .................. 2013-150999

(51) Int. Cl.
*D21H 17/08*   (2006.01)
*C08J 7/04*   (2006.01)
(Continued)

(52) U.S. Cl.
CPC ............. *D21H 17/08* (2013.01); *B01D 71/10* (2013.01); *B01D 71/80* (2013.01); *B32B 23/08* (2013.01);
(Continued)

(58) Field of Classification Search
USPC ........... 162/158, 164.6, 168.2, 157.1, 157.6, 162/157.7
See application file for complete search history.

(56) References Cited

U.S. PATENT DOCUMENTS

2003/0083427 A1   5/2003   Doi et al.
2015/0167249 A1   6/2015   Ono et al.

FOREIGN PATENT DOCUMENTS

EP    1 769 836 A1   4/2007
EP    2 460 934 A1   6/2012
(Continued)

OTHER PUBLICATIONS

International Search Report from the Japanese Patent Office and Written Opinion from the International Searching Authority dated Oct. 21, 2014, directed to International Application No. PCT/JP2014/069248; 9 pages.
(Continued)

*Primary Examiner* — Dennis R Cordray
(74) *Attorney, Agent, or Firm* — Finnegan, Henderson, Farabow, Garrett & Dunner, LLP

(57) ABSTRACT

The present invention provides a fine cellulose fiber sheet, of which various properties and functions such as paper making ability, solvent resistance, adhesion, functionalization agent immobilization, surface zeta potential, hydrophilicity, hydrophobicity, and air permeation resistance are finely controlled, through a process having low environmental impact. A fine cellulose fiber sheet according to the present invention fulfills all of the following requirements (1) to (3): (1) comprises fine cellulose fibers having an average fiber diameter of 2 nm or greater and 1000 nm or less; (2) the weight ratio of the fine cellulose fibers is 50 wt % or greater and 99 wt % or less; and (3) the block polyisocyanate
(Continued)

aggregate content as a weight ratio is 1 to 100 wt % of the weight of the fine cellulose fibers.

19 Claims, 1 Drawing Sheet

(51) Int. Cl.
| | |
|---|---|
| B01D 71/10 | (2006.01) |
| C12M 1/00 | (2006.01) |
| F28F 21/00 | (2006.01) |
| B01D 71/80 | (2006.01) |
| C09D 101/02 | (2006.01) |
| C09K 5/14 | (2006.01) |
| D21H 11/18 | (2006.01) |
| D21H 17/07 | (2006.01) |
| B32B 23/08 | (2006.01) |
| B32B 27/30 | (2006.01) |
| D21H 17/46 | (2006.01) |
| D21H 19/24 | (2006.01) |
| D21H 19/34 | (2006.01) |
| D21H 21/52 | (2006.01) |

(52) U.S. Cl.
CPC ............ *B32B 27/306* (2013.01); *C08J 7/047* (2013.01); *C09D 101/02* (2013.01); *C09K 5/14* (2013.01); *C12M 23/20* (2013.01); *D21H 11/18* (2013.01); *D21H 17/07* (2013.01); *D21H 17/46* (2013.01); *D21H 19/24* (2013.01); *D21H 19/34* (2013.01); *D21H 21/52* (2013.01); *F28F 21/00* (2013.01); *B32B 2307/7242* (2013.01); *B32B 2307/7265* (2013.01); *B32B 2307/73* (2013.01); *B32B 2554/00* (2013.01); *C08J 2300/00* (2013.01); *C08J 2401/02* (2013.01)

(56) References Cited

FOREIGN PATENT DOCUMENTS

| | | |
|---|---|---|
| JP | 62-206099 | 9/1987 |
| JP | 10-95803 | 4/1998 |
| JP | 11-189999 | 7/1999 |
| JP | 11-209401 | 8/1999 |
| JP | 2003-138497 | 5/2003 |
| JP | 2012-46843 | 3/2012 |
| JP | 2012-116905 | 6/2012 |
| JP | 2012-167406 | 9/2012 |
| JP | 2014-24928 | 2/2014 |
| WO | WO 2007/120341 A2 | 10/2007 |
| WO | WO 2009/127819 A1 | 10/2009 |
| WO | WO-2014/014099 | 1/2014 |

OTHER PUBLICATIONS

Notification of Transmittal of Translation of the International Preliminary Report on Patentability from the International Bureau dated Jan. 28, 2016, directed to International Application No. PCT/JP2014/069248; 9 pages.

European search report from the European Patent Office for counterpart European Application No. EP 14 82 5929 dated May 20, 2016.

Communication pursuant to Article 94(3) EPC from the European Patent Office for counterpart European Application No. EP 14 825 929.4 dated Jun. 3, 2016.

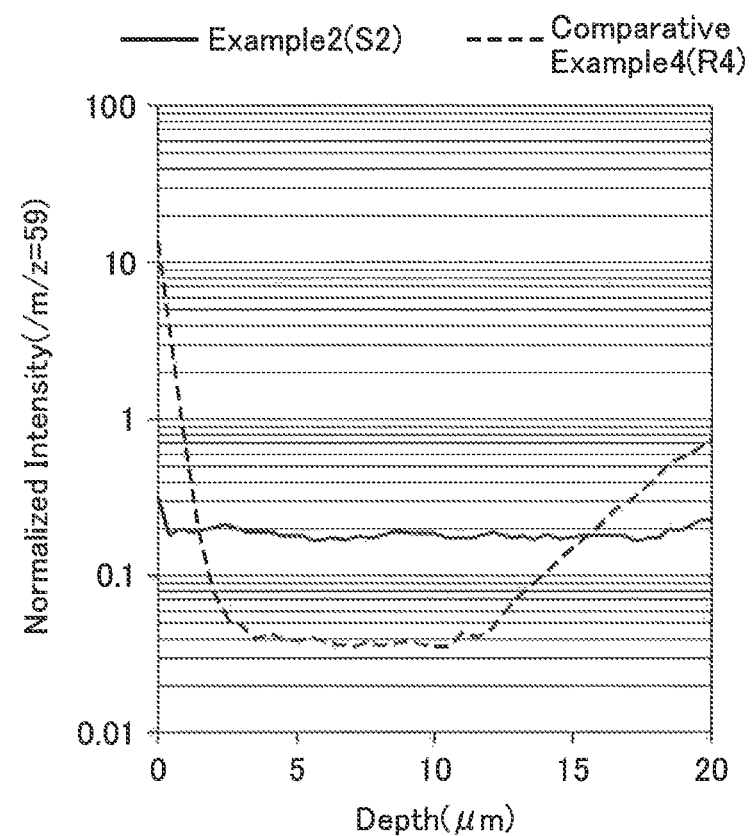

FINE CELLULOSE FIBER SHEET

CROSS-REFERENCE TO RELATED APPLICATIONS

This application is a national phase application of International Application No. PCT/JP2014/069248, filed Jul. 18, 2014, which claims priority to Japanese Application No. 2013-150999, filed Jul. 19, 2013, the content of each is incorporated herein by reference.

TECHNICAL FIELD

The present invention relates to a fine cellulose fiber sheet containing a blocked polyisocyanate aggregate in the sheet. More particularly, the present invention relates to a sheet in which a crosslinked structure is formed by all or a portion of a blocked polyisocyanate chemically bonding with fine cellulose fibers as a result of heat-treating the fine cellulose fiber sheet.

BACKGROUND ART

Attention is currently being focused on fine cellulose fibers in which cellulose-based fibers are beaten and crushed at a high level to increase their fineness (fibrillate) to a fiber diameter of 1 μm or less. Sheets composed of fine cellulose fibers produced in a process consisting of forming a papermaking slurry of these fine cellulose fibers into paper followed by drying are expected to be applied to a wide range of applications in addition to conventional paper. For example, sheets controlled to be porous can be used as filters or membranes having extremely fine pores of 1 μm or less, enabling them to efficiently capture fine particles in a liquid or gas with low pressure loss, and can be used in fine filtration filters or virus removal filters and the like. Moreover, the pores of a porous sheet can be filled in with resin and compounded, enabling it to be used as a flexible, transparent resin sheet having a low coefficient of thermal expansion. On the other hand, transparent, highly dense sheets free of pores can be used as flexible electronic paper or gas barrier membranes and the like.

The water resistance of this fine cellulose fiber sheet is an important technical factor in terms of using in a wide range of applications. Since fine cellulose fiber sheets conventionally retain a sheet structure by hydrogen bonding between fine cellulose short fibers, the hydrogen bonds are easily cleaved and the sheet structure easily collapses as a result of contact with water. Thus, making these fine cellulose fiber sheets water resistant is essential for their use as water treatment filters and in other environments involving contact with water.

Two methods have been reported thus far as techniques used to enhance water resistance, consisting of i) post-processing and ii) internal addition of a water resistance agent.

The post-processing method is a method consisting of impregnating a deposited fine cellulose fiber sheet with an organic solvent containing a crosslinking agent followed by heat treatment. In the following Patent Document 1 according to the present applicant, water resistance is imparted by impregnating with a toluene solution containing 1,6'-hexamethylene diisocyanate or 4,4'-diphenylmethane diisocyanate. However, this technique is extremely disadvantageous from the viewpoints of industrial production and environmental issues since it uses an organic solvent. Even if a water-soluble or water-dispersible water resistance agent is used as a way of solving the aforementioned problems associated with organic solvents, there is an extremely high likelihood of the sheet tearing during treatment due to inadequate wet paper strength. Moreover, it is theoretically difficult to uniformly distribute the water resistance agent in the sheet, making this technique disadvantageous in terms of improving water resistance and other properties.

On the other hand, the internal addition method is a technique by which a water-soluble or water-dispersible water resistance agent is added to a cellulose fiber slurry to prepare a mixed liquid followed by forming into paper, drying and subjecting to heat treatment. In comparison with the post-processing method, the internal addition method is superior in terms of i) having fewer steps, (ii) not using an organic solvent, and (iii) allowing the water resistance agent to be more uniformly dispersed.

Patent Document 2 indicated below discloses a technique for imparting water resistance by using an aqueous emulsion of a polymer having a low glass transition point as a water resistance agent to form a polymer coating on the surface of fine cellulose fibers having a fiber width of 2 nm to 1000 nm followed by compounding with a resin.

In addition, Patent Document 3 indicated below discloses a technique for imparting water resistance in the production of paper using ordinary pulp in the form of needle bleached kraft pulp (NBKP) by using a thermal reaction type, water-soluble urethane prepolymer as a water resistance agent and chemically crosslinking cellulose fibers with the thermal reaction type, water-soluble urethane prepolymer. Differing from the polymer coating having a melting point of Patent Document 2, the use of chemical crosslinking makes it possible to prevent elution into organic solvent while also enabling use in an environment at a temperature equal to or higher than the melting point of the polymer.

Fine cellulose fiber sheets that contribute to industrial use are required to be sheets in which not only water resistance, but also various other properties and functions (such as papermaking ability, solvent resistance, adhesion, functionalization agent immobilization, surface zeta potential, hydrophilicity/hydrophobicity or air permeability resistance) are simultaneously controlled. However, although the aforementioned patent documents contain descriptions regarding imparting water resistance, there is no mention made regarding other properties and functions. Namely, there is currently no technology for producing a fine cellulose fiber sheet in which multiple properties and functions, including water resistance, are controlled.

Moreover, in the case of considering industrial productivity as well as environmental considerations that have come to be required in recent years, there has been a desire to achieve a technique for precisely controlling the aforementioned properties and functions that employs a labor-saving process while having a low impact on the environment.

PRIOR ART DOCUMENTS

Patent Documents

Patent Document 1: Japanese Unexamined Patent Publication No. 2012-46843
Patent Document 2: Japanese Unexamined Patent Publication No. 2012-116905
Patent Document 3: Japanese Unexamined Patent Publication No. 2003-138497

DISCLOSURE OF THE INVENTION

Problems to be Solved by the Invention

An object of the present invention is to provide a process for producing a fine cellulose fiber sheet, in which various properties and functions such as papermaking ability, solvent resistance, adhesion, functionalization agent immobilization, surface zeta potential, hydrophilicity/hydrophobicity or air permeability resistance are precisely controlled, while having a low impact on the environment.

Means for Solving the Problems

As a result of conducting extensive studies and experimentation to solve the aforementioned problems, the inventors of the present invention found that, in a sheet composed of fine cellulose fibers, the aforementioned problems can be solved by providing a sheet in which fine cellulose fibers are crosslinking with a blocked polyisocyanate, thereby leading to completion of the present invention. Namely, the present invention is as described below.

[1] A fine cellulose fiber sheet that fulfills all of the following requirements (1) to (3):

(1) it comprises fine cellulose fibers having an average fiber diameter of 2 nm to 1000 nm and a blocked polyisocyanate aggregate;

(2) the weight ratio of the fine cellulose fibers is 50% by weight to 99% by weight; and, (3) the weight ratio of a blocked polyisocyanate aggregate to the fine cellulose fibers is 1% by weight to 100% by weight.

[2] The fine cellulose fiber sheet described in [1] above, wherein a cationic group is introduced into the blocked polyisocyanate aggregate.

[3] The fine cellulose fiber sheet described in [1] or [2] above, wherein all or a portion of the blocked polyisocyanate aggregate is chemically bound to the fine cellulose fibers to form a crosslinked structure.

[4] A fine cellulose fiber sheet that fulfills all of the following requirements (1) to (4):

(1) it comprises of fine cellulose fibers having an average fiber diameter of 2 nm to 1000 nm and a blocked polyisocyanate aggregate;

(2) the weight ratio of the fine cellulose fibers is 50% by weight to 99% by weight;

(3) a blocked polyisocyanate is uniformly distributed in the sheet in the planar direction and thickness direction; and, (4) the weight ratio of the blocked polyisocyanate to the fine cellulose fibers is 1% by weight to 100% by weight.

[5] The fine cellulose fiber sheet described in [4] above, wherein the blocked polyisocyanate is chemically bound to the fine cellulose fibers.

[6] The fine cellulose fiber sheet described in [4] or [5] above, wherein a cationic group is introduced in the blocked polyisocyanate.

[7] The fine cellulose fiber sheet described in any of [4] to [6] above, wherein the blocked polyisocyanate is a blocked polyisocyanate aggregate.

[8] The fine cellulose fiber sheet described in any of [3] and [5] to [7] above, wherein at least one type of functionalization agent selected from the group consisting of a water-repellent oil processing agent, water-soluble polymer, antimicrobial polymer, thermoplastic resin, thermosetting resin and photocurable resin is immobilized inside and/or on the surface of a fine cellulose fiber layer by the blocked polyisocyanate.

[9] A laminated structure in which the fine cellulose fiber sheet described in any of [1] to [8] and a sheet composed of an organic polymer are laminated.

[10] The laminated structure described in [9] above, wherein the fine cellulose fiber sheet and the sheet composed of an organic polymer are chemically crosslinked by the blocked polyisocyanate.

[11] The laminated structure described in [10] above, wherein a hydrophilic compound is contained in the laminated structure at 1% by weight to 50% by weight as the weight ratio of the laminate.

[12] The laminated structure described in [11] above, wherein the hydrophilic compound contains at least one type of compound selected from inorganic salts consisting of lithium chloride, calcium chloride and magnesium chloride, carboxymethyl cellulose, carboxyethyl cellulose, hydroxyalkyl cellulose and salts or crosslinked products thereof, and organic compounds consisting of polyethylene glycol, polypropylene glycol and polyvinyl alcohol.

[13] An aqueous dispersion for coating or papermaking comprising fine cellulose fibers and a water-dispersible blocked polyisocyanate.

[14] The aqueous dispersion for coating or papermaking described in [13] above, wherein the water-dispersible blocked polyisocyanate is cationic.

[15] The aqueous dispersion for coating or papermaking described in [13] or [14] above, wherein the fiber diameter of the fine cellulose fibers is 2 nm to 1000 nm.

[16] The aqueous dispersion for coating or papermaking described in any of [13] to [15] above, containing at least one type of water-soluble or water-dispersible functionalization agent selected from the group consisting of a water-repellent oil processing agent, water-soluble polymer, antimicrobial polymer, thermoplastic resin, thermosetting resin and photocurable resin.

[17] A method for producing the fine cellulose fiber sheet described in [1], [2] or [4], comprising the following steps:

a preparation step for preparing the aqueous dispersion described in any of [13] to [16] above, a papermaking step for dehydrating the aqueous dispersion by filtration and forming a moisture-containing sheet, and a step for drying the moisture-containing sheet.

[18] A method for producing the fine cellulose fiber sheet described in [3] and any of [5] to [8] above, comprising the following steps:

a preparation step for preparing the aqueous dispersion described in any of [13] to [16] above, a papermaking step for dehydrating the aqueous dispersion by filtration and forming a moisture-containing sheet, a step for drying the moisture-containing sheet, and a heating step for heating the dried sheet.

[19] A method for producing the laminated structure described in [9] above, comprising the following steps:

a preparation step for preparing the aqueous dispersion described in any of [13] to [16] above, a papermaking step for dehydrating the aqueous dispersion on a sheet composed of an organic polymer by filtration and forming a moisture-containing laminated structure in which a fine cellulose fiber layer is laminated on a sheet composed of the organic polymer, and a step for drying the moisture-containing laminated structure.

[20] A method for producing the laminated structure described in any of [10] to [12] above, comprising the following steps:

a preparation step for preparing the aqueous dispersion described in any of [13] to [16] above, a papermaking step for dehydrating the aqueous dispersion on a sheet composed of an organic polymer by filtration and forming a moisture-containing laminated structure in which a fine cellulose fiber layer is laminated on a sheet composed of the organic polymer, a step for drying the moisture-containing laminated structure, and a heating step for heating the dried laminated structure.

[21] A water treatment membrane comprising the fine cellulose fiber sheet described in any of [1] to [8] above or the laminated structure described in [9] or [10] above.

[22] A separation membrane comprising the fine cellulose fiber sheet described in any of [1] to [8] above or the laminated structure described in [9] or [10] above.

[23] A cell culture sheet comprising the fine cellulose fiber sheet described in any of [1] to [8] above or the laminated structure described in [9] or [10] above.

[24] A structure composed of a fiber-reinforced plastic comprising the fine cellulose fiber sheet described in any of [i] to [8] above or the laminated structure described in [9] or [10] above.

[25] A total heat exchanger sheet comprising the fine cellulose fiber sheet described in any of [1] to [8] above or the laminated structure described in any of [9] to [12] above.

[26] The total heat exchanger sheet described in [25] above, wherein the average thickness of the laminated structure is 10 μm to 100 μm.

[27] A total heat exchange element in which the total heat exchanger sheet described in [25] or [26] above is used as a partition that divides two types of air flow having different temperature, different humidity or both.

[28] A total heat exchanger that uses the total heat exchange element described in [27] above.

Effects of the Invention

The fine cellulose fiber sheet containing a blocked polyisocyanate of the present embodiment allows the obtaining of a water resistant sheet by chemically crosslinking the isocyanate with fine cellulose fibers by heat treatment. In addition, according to the present invention, a sheet can be obtained in which various properties and functions such as papermaking ability, solvent resistance, adhesion, functionalization agent immobilization, surface zeta potential, hydrophilicity/hydrophobicity or air permeability resistance are simultaneously and precisely controlled in a film deposition process.

BRIEF DESCRIPTION OF THE DRAWINGS

FIG. 1 is a graph indicating the relationship between variations in C1/C2 in the depth direction in a sample S2 analyzed by time-of-flight secondary ion mass spectrometry (TOF-SIMS).

EMBODIMENTS FOR CARRYING OUT THE INVENTION

The following provides a detailed explanation of the present invention. The fine cellulose fiber sheet of the present embodiment is composed of fine cellulose fibers having an average fiber diameter of 2 nm to 1000 nm.

Here, the average fiber diameter of fine cellulose fibers refers to the number average fine diameter observed in SEM images or TEM images of the surface thereof, and complies with the evaluation means described in the description of International Publication No. WO 2006/4012. If the average fiber diameter of the fine cellulose fibers is less than 2 nm, the fibers dissolve in water as cellulose molecules. Thus, properties of the fibers as fine fibers (strength, rigidity and dimensional stability) are not demonstrated and the fibers cannot be used as fine cellulose fibers for fabricating a sheet. On the other hand, in the case the average fiber diameter of the fine cellulose fibers exceeds 1000 nm, a fine, uniform network structure is unable to be formed and sheet properties become unstable, thereby making this undesirable. From the viewpoints of retaining sheet strength and dimensional stability as well as the formation of a fine, uniform pore diameter, the number average fiber diameter of the fine cellulose fibers is more preferably 10 nm to 500 nm. Furthermore, cellulose fibers having a maximum fiber diameter of 1000 nm or less that compose the fine cellulose fiber sheet of the present invention are fine fibers in the form of short fibers (staple fibers) and do not contain endless long fibers (filaments).

The fine cellulose fiber layer of the present embodiment is preferably composed of a fine cellulose fiber non-woven fabric consisting of fine cellulose fibers having a degree of polymerization (DP) of 100 to 12,000. Degree of polymerization is the number of repeating glucose rings that form the cellulose molecular chain. Tensile strength and modulus of elasticity of the fibers per se are improved by making the degree of polymerization of the cellulose fibers to be 100 or more. As a result, sheet strength and sheet handling improve dramatically, thereby, for example, inhibiting tearing when pleating a water treatment filter or rupturing of a filter during a filtration process. Although there are no particular limitations on the upper limit of the degree of polymerization, in practical terms, cellulose having a degree of polymerization in excess of 12,000 is difficult to acquire and cannot be used industrially. From the viewpoints of handling ease and industrial use, the degree of polymerization of the cellulose fibers is preferably 150 to 8,000 and more preferably 300 to 6,000.

The fine cellulose fibers that compose the fine cellulose fiber sheet of the present embodiment may be chemically modified. Examples thereof include esterified fibers in which all or a portion of hydroxyl groups present on the surface of the fine cellulose include an acetic acid ester, nitric acid ester or sulfuric acid ester, etherified fibers in which all or a portion of the hydroxyl groups include an alkyl ether represented by methyl ether, a carboxyether represented by carboxymethyl ether, or a cyanoether, and fibers in which hydroxyl groups at position 6 of the glucose rings have been oxidized to carboxyl groups (including acid types and basic types) by a TEMPO oxidation catalyst.

The weight ratio of the fine cellulose fibers in the fine cellulose fiber sheet of the present embodiment is 50% by weight to 99% by weight. If the weight ratio of the fine cellulose fibers is less than 50% by weight, since it becomes difficult to form a uniform micropore diameter, a large number of coarse pinholes form, and due to a decrease in specific surface area, capturing efficiency as a water treatment filter decreases considerably. In addition, the characteristic heat resistance and flexibility of cellulose are lost. On the other hand, if the weight ratio of the aforementioned fine cellulose fibers exceeds 99% by weight, mechanical strength and water resistance decrease and handling ease becomes inferior. The weight ratio of the fine cellulose fibers in the sheet of the present invention is preferably 70% by weight to 95% by weight and more preferably 80% by weight to 90% by weight.

The fine cellulose fiber sheet of the present embodiment is characterized in that it contains a blocked polyisocyanate. A blocked polyisocyanate refers to (1) that having a basic structure consisting of polyisocyanate and a polyisocyanate compound such as a polyisocyanate derivative, (2) that in which isocyanate groups are blocked by a blocking agent, (3) that which does not react with functional groups having an active hydrogen at normal temperatures, and (4) that in which blocking groups are eliminated and active isocyanate groups are regenerated by heat treatment at a temperature equal to or higher than the temperature at which blocks dissociate, and bonds are formed by reacting with functional groups containing an active hydrogen. Furthermore, the polyisocyanate of the present embodiment refers to a multifunctional isocyanate having two or more isocyanate groups. Similarly, a blocked polyisocyanate refers to a polyisocyanate in which isocyanate groups have been blocked by a blocking agent for the purpose of inhibiting reactions with water in an aqueous environment, or in other words, a blocked multifunctional isocyanate or blocked-type multifunctional isocyanate.

Since ordinary isocyanate compounds not having a blocking group easily react with water, they cannot be added to a papermaking slurry. However, since blocked polyisocyanates do not react with water in a papermaking slurry, they can be added to a papermaking slurry. Moreover, reaction of an isocyanate compound with water in wet paper can be prevented by drying the wet paper at a temperature equal to or lower than the dissociation temperature of the blocking agent. By then subjecting the resulting dried sheet to heat treatment at a temperature equal to or higher than the dissociation temperature of the blocking agent, in addition to undergoing self-curing, the blocked polyisocyanate effectively forms covalent bonds with functional groups (such as hydroxyl groups, amino groups, carboxyl groups or thiol groups) present on the surface of the fine cellulose fibers and organic polymer sheet. As a result, this leads to an improvement of water resistance of the fine cellulose fiber sheet. In addition, the blocked polyisocyanate also fulfills an important role in terms of precisely controlling various properties and functions such as papermaking ability, solvent resistance, adhesion, functionalization agent immobilization, surface zeta potential, hydrophilicity/hydrophobicity or air permeability resistance.

There are no particular limitations on the blocked polyisocyanate used in the present invention provided it contains at least two isocyanate groups. In addition, examples of the basic structure of the blocked polyisocyanate include aromatic polyisocyanates, alicyclic polyisocyanates and aliphatic polyisocyanates. Among these, alicyclic polyisocyanates and aliphatic polyisocyanates are more preferable from the viewpoint of reduced yellowing.

Examples of aromatic polyisocyanate raw materials include aromatic diisocyanates such as 2,4-tolylene diisocyanate, 2,6-tolylene diisocyanate and mixtures thereof (TDI), diphenylmethane-4,4'-diisocyanate (MDI), naphthalene-1,5-diisocyanate, 3,3-dimethyl-4,4-biphenylene diisocyanate, crude TDI, polymethylene polyphenyl diisocyanate, crude MDI, phenylene diisocyanate or xylylene diisocyanate.

Examples of alicyclic polyisocyanate raw materials include alicyclic diisocyanates such as 1,3-cyclopentane diisocyanate, 1,3-cyclopentene diisocyanate or cyclohexane diisocyanate.

Examples of aliphatic polyisocyanates include aliphatic diisocyanates such as trimethylene diisocyanate, 1,2-propylene diisocyanate, butylene diisocyanate, pentamethylene diisocyanate or hexamethylene diisocyanate.

Examples of polyisocyanate derivatives serving as the basic structure of the blocked polyisocyanate include the aforementioned polyisocyanate oligomers (such as dimers, trimers, pentamers or heptamers) as well as compounds obtained by reacting one or two types thereof with an active hydrogen-containing compound. Examples of these compounds include allophanate modification products (such as allophanate modification products formed by reacting a polyisocyanate with an alcohol), polyol modification products (such as polyol modification products (alcohol adducts) formed by reacting a polyisocyanate with an alcohol), biuret modification products (such as biuret modification products formed by reaction a polyisocyanate with water or an amine), urea modification products (such as urea modification products formed by reacting a polyisocyanate with a diamine), oxadiazinetrione modification products (such as oxadiazinetrione modification products formed by reacting a polyisocyanate with carbon dioxide gas), carbodiimide modification products (such as carbodiimide modification products formed by a decarboxylation condensation reaction of a polyisocyanate), uretdione modification products and uretonimine modification products.

Examples of active hydrogen-containing compounds include monovalent to hexavalent hydroxyl group-containing compounds including polyester polyols and polyether polyols, amino group-containing compounds, thiol group-containing compounds and carboxyl group-containing compounds. In addition, water or carbon dioxide and the like present in the air or reaction field are also included.

Examples of monovalent to hexavalent alcohols (polyols) include unpolymerized polyols and polymerized polyols. Unpolymerized polyols refer to polyols not having been previously polymerized, while polymerized polyols refer to polyols that are obtained by polymerizing a monomer.

Examples of unpolymerized polyols include monoalcohols, diols, triols and tetraols. There are no particular limitations on monoalcohols, and examples thereof include methanol, ethanol, n-propanol, i-propanol, n-butanol, i-butanol, s-butanol, n-pentanol, n-hexanol, n-octanol, n-nonanol, 2-ethylbutanol, 2,2-dimethylhexanol, 2-ethylhexanol, cyclohexanol, methylcyclohexanol and ethylcyclohexanol. There no particular limitations on diols, and examples thereof include ethylene glycol, diethylene glycol, triethylene glycol, propylene glycol, dipropylene glycol, tripropylene glycol, 1,2-propanediol, 1,3-propanediol, 1,2-butanediol, 1,3-butanediol, 1,4-butanediol, 2,3-butanediol, 2-methyl-1,2-propanediol, 1,5-pentanediol, 2-methyl-2,3-butanediol, 1,6-hexanediol, 1,2-hexanediol, 2,5-hexanediol, 2-methyl-2,4-pentanediol, 2,3-dimethyl-2,3-butanediol, 2-ethylhexanediol, 1,2-octanediol, 1,2-decanediol, 2,2,4-trimethylpentanediol, 2-butyl-2-ethyl-1,3-propanediol, 2,2-diethyl-1,3-propanediol, phloroglucin, pyrogallol, catechol, hydroquinone, bisphenol A, bisphenol F and bisphenol S. There are no particular limitations on triols, and examples thereof include glycerin and trimethylolpropane. In addition, there are no particular limitations on tetraols, and examples thereof include pentaerythritol, 1,3,6,8-tetrahydroxynaphthalene and 1,4,5,8-tetrahydroxyanthracene.

There are no particular limitations on the polymerized polyols, and examples thereof include polyester polyols, polyether polyols, acrylic polyols and polyolefin polyols.

There are no particular limitations on the polyester polyols, and examples thereof include polyester polyols obtained by a condensation reaction between a dicarboxylic acid such as succinic acid, adipic acid, sebacic acid, dimer acid, maleic anhydride, phthalic anhydride, isophthalic acid or terephthalic acid, either alone or as a mixture thereof, and a polyvalent alcohol such as ethylene glycol, propylene glycol, diethylene glycol, neopentyl glycol, trimethylolpropane or glycerin, either alone or as a mixture thereof, and polycaprolactones obtained by ring-opening polymerization of ε-caprolactone using a polyvalent alcohol.

There are no particular limitations on the polyether polyols, and examples thereof include polyether polyols obtained by random or block addition of an alkylene oxide such as ethylene oxide, propylene oxide, butylene oxide, cyclohexene oxide or styrene oxide, either alone or as a mixture thereof, to a polyvalent hydroxy compound, either alone or as a mixture thereof, using a hydroxide of lithium, sodium or potassium, a strongly basic catalyst such as an alcoholate or alkyl amine, or a compound metal cyanide complex such as metalloporphyrin or hexacyanocobalt zinc complex, and polyether polyols obtained by reacting alkylene oxide with a polyamine compound such as ethylenediamine. Examples also include so-called polymer polyols obtained by polymerizing an acrylamide and the like using these polyethers as catalysts.

Examples of the aforementioned polyvalent alcohol compounds include:

1) diglycerin, ditrimethylolpropane, pentaerythritol or dipentaerythritol, 2) sugar-alcohol-based compounds such as erythritol, D-threitol, L-arabinitol, ribitol, xylitol, sorbitol, mannitol, galactitol or rhamnitol, 3) monosaccharides such as arabinose, ribose, xylose, glucose, mannose, galactose, fructose, sorbose, rhamnose, fucose or ribodesose, 4) disaccharides such as trehalose, sucrose, maltose, cellobiose, gentiobiose, lactose or melibiose, 5) trisaccharides such as raffinose, gentianose or melezitose, and 6) tetrasaccharides such as stachyose.

Examples of acrylic polyols include acrylic polyols having as an essential component thereof a compound, either alone or as a mixture thereof, selected from the group consisting of acrylic acid esters having an active hydrogen such as 2-hydroxyethyl acrylate, 2-hydroxypropyl acrylate or 2-hydroxybutyl acrylate, acrylic acid monoesters or methacrylic acid monoesters of glycerin, acrylic acid monoesters or methacrylic acid monoesters of trimethylolpropane, and methacrylic acid esters having an active hydrogen such as 2-hydroxyethyl methacrylate, 2-hydroxypropyl methacrylate, 2-hydroxybutyl methacrylate, 3-hydroxypropyl methacrylate or 4-hydroxybutyl methacrylate, which are obtained by polymerizing in the presence or absence of a compound, either alone or as a mixture thereof, selected from the group consisting of acrylic acid esters such as methyl acrylate, ethyl acrylate, isopropyl acrylate, n-butyl acrylate or 2-ethylhexyl acrylate, methacrylic acid esters such as methyl methacrylate, ethyl methacrylate, isopropyl methacrylate, n-butyl methacrylate, isobutyl methacrylate, n-hexyl methacrylate or lauryl methacrylate, unsaturated carboxylic acids such as acrylic acid, methacrylic acid, maleic acid or itaconic acid, unsaturated amides such as acrylamide, n-methylolacrylamide or diacetone acrylamide, and other polymerizable monomers such as vinyl monomers having a hydrolyzable silyl group such as glycidyl methacrylate, styrene, vinyl toluene, vinyl acetate, acrylonitrile, dibutyl fumarate, vinyl trimethoxysilane, vinyl methyl dimethoxysilane or γ-methacryloxypropyl methoxysilane.

Examples of polyolefin polyols include polybutadiene having two or more hydroxyl groups, hydrogenated polybutadiene, polyisoprene and hydrogenated polyisoprene. Moreover, monoalcohol compounds having 50 or fewer carbon atoms in the form of isobutanol, n-butanol or 2-ethylhexanol and the like can be used in combination therewith.

Examples of amino group-containing compounds include monohydrocarbylamines having 1 to 20 carbon atoms (such as alkyl amines (e.g., butylamine), benzylamine or aniline), aliphatic polyamines having 2 to 20 carbon atoms (such as ethylenediamine, hexamethylenediamine or diethylenetriamine), alicyclic polyamines having 6 to 20 carbon atoms (such as diaminocyclohexane, dicyclohexylmethanediamine or isophoronediamine), aromatic polyamines having 2 to 20 carbon atoms (such as phenylenediamine, tolylenediamine or diphenylmethanediamine), polycyclic polyamines having 2 to 20 carbon atoms (such as piperazine or N-aminoethylpiperazine), alkanolamines (such as monoethanolamine, diethanolamine or triethanolamine), polyamide polyamines, polyether amines and hydrazine obtained by condensing a dicarboxylic acid with an excess of polyamine (such as hydrazine or monoalkylhydrazines), dihydrazides (such as succinic dihydrazide or terephthalic dihydrazide), guanidines (such as butylguanidine or 1-cyanoguanidine) and dicyandiamides.

Examples of thiol group-containing compounds include monovalent thiol compounds having 1 to 20 carbon atoms (such as alkyl thiols such as ethyl thiol, phenyl thiol or benzyl thiol), and polyvalent thiol compounds (such as ethylenedithiol or 1,6-hexanedithiol).

Examples of carboxyl group-containing compounds include monovalent carboxylic acid compounds (such as alkyl carboxylic acids such as acetic acid, or aromatic carboxylic acids such as benzoic acid), and polyvalent carboxylic acid compounds (such as alkyl dicarboxylic acids such as oxalic acid or malonic acid or aromatic dicarboxylic acids such as terephthalic acid).

The blocking agent is added to isocyanate groups of a polyisocyanate compound to block those groups. Although this blocking agent is stable at normal temperatures, the blocking agent dissociates enabling the regeneration of free isocyanate groups when heated to a heat treatment temperature (normally about 100° C. to about 200° C.).

Examples of blocking agents that satisfy such requirements include: (1) alcohols such as methanol, ethanol, 2-propanol, n-butanol, sec-butanol, 2-ethyl-1-hexanol, 2-methoxyethanol, 2-ethoxyethanol or 2-butoxyethanol, (2) alkyl phenol-based blocking agents: mono- and dialkyl phenols having as a substituent thereof an alkyl group having 4 or more carbon atoms, examples of which include monoalkyl phenols such as n-propyl phenol, sec-butyl phenol, t-butyl phenol, n-hexyl phenol, 2-ethylhexyl phenol, n-octyl phenol or n-nonyl phenol, and dialkyl phenols such as di-n-propyl phenol, diisopropyl phenol, isopropyl cresol, di-n-butyl phenol, di-t-butyl phenol, di-sec-butyl phenol, di-n-octyl phenol, di-2-ethylhexyl phenol or di-n-nonyl phenol, (3) phenol-based blocking agents: phenol, cresol, ethyl phenol, styrenated phenol and hydroxybenzoic acid esters, (4) active methylene-based blocking agents: dimethyl malonate, diethyl malonate, methyl acetoacetate, ethyl acetoacetate and acetyl acetone, (5) mercaptan-based blocking agents: butyl mercaptan and dodecyl mercaptan, (6) acid amide-based blocking agents: acetanilide, acetic acid amide, ε-caprolactam, δ-valerolactam and γ-butyrolactam, (7) acid imide-based blocking agents: succinic acid imide and maleic acid imide, (8) imidazole-based blocking agents: imidazole, 2-methylimidazole, 3,5-dimethylpyrazole and 3-methylpyrazole, (9) urea-based blocking agents: urea, thiourea and ethylene urea,

(10) oxime-based blocking agents: formaldoxime, acetoaldoxime, acetoxime, methyl ethyl ketoxime and cyclohexanoxime,

(11) amine-based blocking agents: diphenylamine, aniline, carbazole, di-n-propylamine, diisopropylamine and isopropylethylamine, and these blocking agents can be used alone or two or more types can be used in combination.

A blocked polyisocyanate aggregate in the present invention refers to a coating film finely dispersed within a sheet formed from a blocked polyisocyanate by drying a water-dispersible blocked polyisocyanate. A water-dispersible blocked polyisocyanate refers to a compound in which a hydrophilic compound is directly bonded to a blocked polyisocyanate and emulsified (self-emulsifying type) or that which has been forcibly emulsified with a surfactant and the like (forcibly emulsified type). Emulsions obtained by each method have any of an anionic, nonionic or cationic hydrophilic group exposed on the surface thereof.

Formation of a coating film by the aforementioned water-dispersible blocked polyisocyanate is carried out by going through the following three production steps: (1) a preparation step for preparing a papermaking slurry that is adsorbed to fine cellulose fibers by adding a water-dispersible blocked polyisocyanate, (2) a papermaking step for forming wet paper containing the water-dispersible blocked polyisocyanate by filtering the papermaking slurry with a porous base material, and (3) a drying step for obtaining a dry sheet by drying the wet paper. In this drying step, the water-dispersible blocked polyisocyanate is dehydrated together with the formation of a coating film on the fine cellulose fibers.

The following provides a detailed description of the structure of the aforementioned water-dispersible blocked polyisocyanate. Self-emulsifying blocked polyisocyanates have an active hydrogen group-containing compound having an anionic, nonionic or cationic group bound to a blocked polyisocyanate backbone.

Although there are no particular limitations on the active hydrogen group-containing compound having an anionic group, an example thereof is a compound having one anionic group and two or more active hydrogen groups.

Examples of anionic groups include carboxyl groups, sulfonate groups and phosphate groups. Specific examples of active hydrogen group-containing compounds having a carboxyl group include dihydroxycarboxylic acids such as 2,2-dimethylolacetic acid or 2,2-dimethylollactic acid, diaminocarboxylic acids such as 1-carboxy-1,5-pentylenediamine or dihydroxybenzoic acid, and half ester compounds of polyoxypropylene triol and maleic anhydride and/or phthalic anhydride.

In addition, examples of active hydrogen-group containing compounds having a sulfonic acid group include N,N-bis(2-hydroxyethyl)-2-aminoethanesulfonic acid and 1,3-phenylenediamine-4,6-disulfonic acid.

In addition, examples of active hydrogen group-containing compounds having a phosphate group include 2,3-dihydroxypropylphenylphosphate.

In addition, examples of active hydrogen group-containing compounds having a betaine structure-containing group include sulfobetaine group-containing compounds obtained by reacting a tertiary amine such as N-methyldiethanolamine with 1,3-propanesultone.

In addition, these active hydrogen group-containing compounds having an anionic group may be alkylene oxide modification products obtained by adding an alkylene oxide such as ethylene oxide or propylene oxide.

In addition, these active hydrogen group-containing compounds having an anionic group can be used alone or two or more types can be used in combination.

Although there are no particular limitations on the active hydrogen group-containing compound having a nonionic group, ordinary polyalkylene ether polyols containing an alkoxy group for the nonionic group, for example, are used. Ordinary nonionic group-containing polyester polyols, polycarbonate polyols and the like are also used.

Polyols having a number average molecular weight of 500 to 10,000, and particularly 500 to 5,000, are used as high molecular weight polyols.

Although there no particular limitations on the active hydrogen group-containing compound having a cationic group, examples thereof include aliphatic compounds having an active hydrogen-containing group in the manner of a hydroxyl group or primary amino group and a tertiary amino group, such as N,N-dimethylethanolamine, N-methylethanolamine and N,N-dimethylethylenediamine. In addition, N,N,N-trimethylolamine or N,N,N-triethanolamine having a tertiary amine can also be used. Among these, polyhydroxy compounds having a tertiary amine group and containing two or more active hydrogens demonstrating reactivity with isocyanate groups are preferable.

In addition, these active hydrogen group-containing compounds having a cationic group may be alkylene oxide modification products obtained by adding an alkylene oxide such as ethylene oxide or propylene oxide. In addition, these active hydrogen group-containing compounds having a cationic group can be used alone or two or more types can be used in combination.

Cationic groups can be easily made to disperse in water in the form of salts by neutralizing with a compound having an anionic group. Examples of anionic groups include a carboxyl group, sulfonate group and phosphate group. Examples of compounds having a carboxyl group include formic acid, acetic acid, propionic acid, butyric acid and lactic acid, examples of compounds having a sulfonate group include ethanesulfonic acid, and examples of compounds having a phosphate group include phosphoric acid and phosphoric acid esters. Compounds having a carboxyl group are preferable, and acetic acid, propionic acid and butyric acid are more preferable. The equivalent ratio of cationic groups to anionic groups introduced into a blocked polyisocyanate in the case of neutralizing is 1:0.5 to 1:3 and preferably 1:1 to 1:1.5. In addition, an introduced tertiary amine group can also be quaternized with dimethyl sulfate or diethyl sulfate and the like.

The ratio at which a blocked polyisocyanate and the aforementioned active hydrogen group-containing compound are reacted in the present invention in terms of the equivalent ratio of isocyanate groups to active hydrogen groups is within the range of 1.05 to 1000, preferably 2 to 200 and more preferably 4 to 100. If the equivalent ratio is less than 1.05, since the isocyanate content in a hydrophilic polyisocyanate decreases considerably, in addition to the occurrence of a decrease in curing rate of the blocked polyisocyanate and embrittlement of the cured product, the number of crosslinking sites with the fine cellulose fibers decreases, which is not desirable for use as a water resistance agent or immobilizing agent. If the equivalent ratio exceeds 1000, the effect of lowering interfacial tension is no longer adequate and hydrophilicity cannot be demonstrated, thereby making this undesirable. Furthermore, the method used to react a polyisocyanate compound having two or more isocyanate groups in a molecule thereof with an active hydrogen group-containing compound in the present invention consists of mixing the two components and carrying out an ordinary urethanation reaction.

Forcibly emulsified blocked polyisocyanates are compounds that are emulsified and dispersed by a commonly known, ordinary anionic surfactant, nonionic surfactant, cationic surfactant, amphoteric surfactant, polymeric surfactant or reactive surfactant and the like. Among these, anionic surfactants, nonionic surfactants or cationic surfactants are preferable since they are inexpensive and allow the obtaining of favorable emulsification.

Examples of anionic surfactants include alkyl carbonate-based compounds, alkyl sulfate-based compounds and alkyl phosphates.

Examples of nonionic surfactants include ethylene oxide and/or propylene oxide adducts of alcohols having 1 to 18 carbon atoms, ethylene oxide and/or propylene oxide adducts of alkyl phenols, and ethylene oxide and/or propylene oxide adducts of alkylene glycols and/or alkylene diamines.

Examples of cationic surfactants include primary to tertiary amines, pyridinium salts, alkyl pyridinium salts and quaternary ammonium salts such as quaternary alkyl halide ammonium salts.

There are no particular limitations on the amount used in the case of using these emulsifiers and they can be used in an arbitrary amount, if the weight ratio thereof based on a value of 1 for the amount of blocked polyisocyanate is smaller than 0.05, there are cases in which adequate dispersibility may not be obtained, while if the amount used exceeds 0.3, since there is the risk of decreases in properties such as water resistance or functionalization agent immobilization, the weight ratio of the amount used is preferably 0.01 to 0.3 and more preferably 0.05 to 0.2.

Furthermore, both the aforementioned auto-emulsifying and forcibly emulsified types of water-dispersible blocked polyisocyanates can be contain up to 20% by weight of a solvent other than water. There are no particular limitations on the solvent in this case, and examples thereof include ethylene glycol monomethyl ether, diethylene glycol monomethyl ether, ethylene glycol, diethylene glycol and triethylene glycol. One type of these solvents may be used alone or two or more types may be used in combination. From the viewpoint of dispersibility in water, the solubility in water as a solvent is preferably 5% by weight or more, and more specifically, dipropylene glycol dimethyl ether and dipropylene glycol monomethyl ether are preferable.

The average dispersed particle diameter of the aforementioned water-dispersed blocked polyisocyanate is required to be 1 nm to 1000 nm, and is preferably 10 nm to 500 nm and more preferably 10 nm to 200 nm.

Although the surface of the aforementioned water-dispersed blocked polyisocyanate may be nonionic or cationic, it is more preferably cationic. The reason for this is that, at the stage of producing a papermaking slurry, in addition to enabling the water-dispersible blocked polyisocyanate (0.0001% by weight to 0.5% by weight) in the dilute fine cellulose fiber slurry (0.01% by weight to 0.5% by weight) to be effectively adsorbed to the fine cellulose fibers, this is also advantageous in terms of utilizing electrostatic interaction. The surface of ordinary cellulose fibers is known to be anionic (Non-Patent Document 1: J. Brandrup (editor) and E. H. Immergut (editor), "Polymer Handbook 3rd Edition", V-153 to V-155). Thus, the surface of the water-dispersible blocked polyisocyanate is more preferably cationic. However, even if the surface is nonionic, fine cellulose fibers can still be adequately adsorbed depending on the polymer chain length or rigidity of hydrophilic groups of the emulsion. Moreover, even in cases in which adsorption is more difficult due to electrostatic repulsion as with an anionic surface, the water-dispersible blocked polyisocyanate can be adsorbed to the fine cellulose fibers by using a commonly known cationic adsorption assistant or cationic polymer.

The fine cellulose fiber sheet of the present embodiment is characterized in that the blocked polyisocyanate and fine cellulose fibers are chemically bound to form a reactant by heat treatment at a temperature at which the blocked groups are eliminated. Chemical bonding refers to the formation of covalent bonds as a result of active isocyanate groups, regenerated by heat treatment at a temperature equal to or higher than the blocked group dissociation temperature, reacting with a functional group having an active hydrogen. An example thereof is urethane bonding occurring due to a reaction with the large number of hydroxyl groups present on the surface of the fine cellulose fibers. In addition, another example is amidourea bonding occurring due to a reaction with carboxyl groups present in a trace amount on the surface of fine cellulose fibers. Moreover, covalent bonds can also be formed by the aforementioned chemically-modified cellulose fibers provided functional groups having an active hydrogen are present on the fiber surface. Examples of functional groups having an active hydrogen include hydroxyl groups, amino groups, thiol groups and carboxyl groups. In addition to improving properties such as tensile strength or wet strength of a sheet as a result of being formed three-dimensionally relative to the fine cellulose fibers, this chemical bonding inhibits elution of blocked polyisocyanate contained in the sheet into organic solvent.

The fine cellulose fiber sheet of the present embodiment is characterized in that a blocked polyisocyanate is uniformly distributed in the planar direction and thickness direction in the sheet. In the present description, the uniform distribution of blocked polyisocyanate in the planar direction and thickness direction in the sheet is defined in the manner indicated below.

Uniformity in the planar direction refers to the ratio (W1/W2) of the amount of blocked polyisocyanate (W1) to the amount of cellulose (W2) at an arbitrary location in the sheet being constant at all times. Being constant refers to variations in W1/W2 at four arbitrary locations in a sheet measuring 25 cm×25 cm having a coefficient of variation of 50% or less.

Uniformity in the thickness direction refers to the ratio of the amount of blocked polyisocyanate to the amount of cellulose in each of the upper, middle and lower portions of a sheet when divided into three equal portions in the direction of thickness each being the same. Being the same in the present invention refers to calculating the average of W1/W2 in the upper portion, the average of W1/W2 in the middle portion and the average of W1/W2 in the lower portion at four arbitrary locations in a sheet measuring 25 cm×25 cm, and the variation in those three average values having a coefficient of variation of 50% or less.

The coefficient of variation of the distribution of polyisocyanate is preferably 50% or less. In the case the coefficient of variation exceeds 50%, properties such as wet tensile strength or biodegradation resistance are inferior in comparison with a sheet in which an equal amount of polyisocyanate is uniformly contained.

Furthermore, coefficient of variation refers to a value that represents relative variation, and can be calculated as indicated below.

Coefficient of variation (CV)=(standard deviation/arithmetic mean)×100

The ratio between the amount of blocked polyisocyanate and the amount of cellulose is determined, for example, from three-dimensional composition analysis by TOF-SIMS with sputter etching. TOF-SIMS can be used to analyze the elemental composition and chemical structure of the polar surface of a sample. When a sample is irradiated with a primary ion beam under ultra-high vacuum, secondary ions are released from the polar surface (1 nm to 3 nm) of the sample. When the secondary ions are then introduced into a time-of-flight (TOF) mass spectrometer, a mass spectrum of the sample polar surface is obtained. At this time, molecular ions that retain a chemical structure and surface components in the form of partially cleaved fragments can be detected by minimizing the irradiated amount of primary ions, and information on elemental composition and chemical structure of the polar surface in the planar direction is obtained. In addition, by repeating sputter etching with a sputter etching gun and measurement of secondary ions with a primary ion gun, information on elemental composition and chemical structure is obtained in the direction of depth, thereby enabling three-dimensional analysis of composition and chemical structure.

Calculation of W1/W2 by TOF-SIMS is carried out, for example, in the manner indicated below. Four locations on a 25 cm×25 cm sheet are randomly selected and samples measuring 1 cm on a side are acquired. Three-dimensional TOF-SIMS composition analysis is then carried out on the four samples. The ratio of the amount of blocked polyisocyanate to the amount of cellulose can be determined from the number of counts (C1) at m/z=26 (fragment ion: CN) derived from the blocked polyisocyanate and the number of counts (C2) at m/z=59 (fragment ion: $C_2H_3O_2$) derived from cellulose in the form of W1/W2=C1/C2. Other fragment ions derived from the blocked polyisocyanate such as CNO (m/z=42) may also be used. In addition, other fragment ions derived from cellulose such as $C_3H_3O_2$ (m/z=71) may also be used. Furthermore, since the fragment ions observed vary according to differences in the composition of the blocked polyisocyanate and raw materials of the cellulose, the fragment ions are not limited to those indicated above.

Examples of measurement conditions used during TOF-SIMS are indicated below.

(Measurement Conditions)
Instrument used: NanoTOF (Ulvac-Phi Inc.)
Primary ion: $Bi_3^{++}$
Accelerating voltage: 30 kV
Ion current: Approx. 0.1 nA (DC)
Analyzed area: 200 μm×200 μm
Analysis time: Approx. 6 sec/cycle
Detected ions: Anions
Neutralization: Use of electron gun
(Sputtering Conditions)
Sputter ion: $Ar2500^+$
Accelerating voltage: 20 kV
Ion current: Approx. 5 nA
Sputtered area: 600 μm×600 μm
Sputtering time: 60 sec/cycle
Neutralization: Use of electron gun The fine cellulose fiber sheet of the present embodiment is characterized in that it contains a blocked polyisocyanate. The amount thereof is preferably such that the weight ratio of the solid content of blocked polyisocyanate is within the range of 1% by weight to 100% by weight based on the weight of cellulose. This weight ratio is more preferably 2% by weight to 70% by weight and even more preferably 3% by weight to 50% by weight. The amount of additives such as a wet strength agent added in the pulp is typically 1% by weight or less. However, in the case of the present embodiment, since the fine cellulose fibers have an extremely large specific surface area, it is not easy to coat the entire surface at 1% by weight of blocked polyisocyanate, thereby preventing the obtaining of described properties such as tensile strength, tensile strength wet/dry ratio or biodegradation resistance. On the other hand, in the case the weight ratio exceeds 100% by weight, since the periphery of the fine cellulose fibers becomes excessively coated with the blocked polyisocyanate, the inherent properties of cellulose, such as high heat resistance and decorativeness, are lost, thereby making this undesirable.

The fine cellulose fiber sheet of the present embodiment preferably has tensile strength corresponding to a basis weight of 10 g/m of 5 N/15 mm or more due to the blocked polyisocyanate contained in the sheet. Although the tensile strength of the sheet is influenced to a certain extent by the basis weight thereof, if the tensile strength corresponding to a basis weight of 10 g/m$^2$ is less than 5 N/15 mm, this leads to tearing of the sheet during handling. The tensile strength is more preferably 7 N/15 mm or more and even more preferably 8 N/15 mm or more (both corresponding to a basis weight of 10 g/m$^2$). On the other hand, although there is no particular upper limit of the tensile strength of the fine cellulose fiber sheet of the present embodiment, it is essentially not possible for tensile strength to exceed 100 N/15 mm per basis weight of 10 g/m$^2$.

Furthermore, in the present description, tensile strength is measured after storing for 24 hours in an environment controlled to a room temperature of 20° C. and humidity of 50% RH.

In addition, one characteristic of the fine cellulose fiber sheet of the present embodiment is its superior wet tensile strength. One application of the present invention in the form of a sheet having a large specific surface area is a liquid filter. It is necessary to have superior wet tensile strength when used in a liquid. More specifically, the ratio of wet tensile strength to dry tensile strength is 50% or more. The wet/dry tensile strength ratio as defined in the present description refers to the value obtained by calculating according to the following equation by defining the tensile strength of a dry sheet under the aforementioned conditions as dry strength, and defining tensile strength measured after immersing the dry sheet in a container filled with an amount of water sufficient for immersing the sheet for 5 minutes as wet strength. Furthermore, dry strength and wet strength are not required to be converted to values corresponding to a basis weight of 10 g/m$^2$.

Wet/dry strength ratio=(wet strength)/(dry strength)×100

Since the tensile strength wet/dry strength ratio of the fine cellulose fiber sheet of the present embodiment is 50% or more, in the case of using as an adsorption filter or cell culture base material that contacts a solution containing water, the sheet is able to maintain and demonstrate stable adsorption effects over a long period of time without tearing. The wet/dry strength ratio of a water-resistant cellulose sheet is preferably 50% or more, and more preferably 60% or more, from the viewpoint of use.

The fine cellulose fiber sheet of the present embodiment may also be highly resistant to biodegradation by cellulase. Cellulase is the generic term for enzyme proteins that catalyze the hydrolysis reaction of β-1,4 glucoside bonds of the cellulose molecular chain. Cellulase is an enzyme protein that is widely dispersed throughout the living world in microorganisms such as bacteria and fungi as well as in insects, and can be easily acquired. Various types of cellulase are known, and can be made to efficiently hydrolyze cellulose to monomer units of cellulose in the form of glucose molecules by selecting the appropriate type thereof. On the other hand, from the viewpoint of providing cellulose-based materials, the presence of cellulase causes significant material deterioration. Thus, it is important to impart biodegradation resistance to cellulase to the fine cellulose fiber sheet of the present embodiment.

One example of a method for quantitatively evaluating the biodegradation resistance to cellulase of the fine cellulose fiber sheet of the present embodiment consists of allowing hydrolysis of cellulose to proceed using a mixture of cellulases including, for example, endoglucanase, exoglucanase and β-glucosidase, and quantifying the amount of glucose present in the reaction liquid. The amount of glucose formed can be quantified according to the glucose oxidase method. Furthermore, glucose can also be quantified using a commercially available kit in the manner of Glucose Test Wako II manufactured by Wako Pure Chemical Industries Ltd. A small amount of glucose formed means that it is difficult for hydrolysis of cellulose to proceed and biodegradation resistance can be said to be high. Namely, glucose yield can be determined using the following equation:

Glucose yield (%)=(amount of glucose formed)/(dry sample weight)×100

Biodegradation resistance index can be evaluated using the following equation.

Biodegradation resistance index=1/(glucose yield/100)

The higher the value of this biodegradation resistance index, the lower the level of biodegradability.

Another application of the fine cellulose fiber sheet of the present embodiment in the form of a water treatment filter also includes use in an environment in which cellulase is present. Thus, the biodegradation resistance of the sheet of the present embodiment is preferably two or more times that of a fine cellulose fiber sheet not containing a blocked polyisocyanate depending on the application.

The fine cellulose fiber sheet of the present embodiment is characterized by being a sheet in which hydrophilicity and hydrophobicity are controlled. The hydrophilicity and hydrophobicity of the sheet have a considerable effect on the coated amount, impregnated amount or ease of coating or impregnation when coating or impregnating a hydrophilic compound or hydrophobic compound on the sheet for a prescribed purpose according to the application, for example. In addition, the sheet may also be applied to a separation membrane by utilizing its hydrophilicity or hydrophobicity. The degree of hydrophobicity of the sheet following heat treatment varies considerably according to the type and added amount of the aforementioned blocked polyisocyanate in particular. Thus, the hydrophilicity and hydrophobicity of the fine cellulose fiber sheet can be controlled according to selection or design of a suitable blocked polyisocyanate.

There are several methods for evaluating hydrophilicity and hydrophobicity, and a method is selected that corresponds to the specific objective. In addition, since hydrophilicity and hydrophobicity are relative indicators, they are determined by comparing with a reference substance. For example, the hydrophilicity and hydrophobicity of a sheet to which has been added blocked polyisocyanate and various types of functionalization agents are evaluated by using a sheet composed only of fine cellulose fibers as a reference substance. An example of an evaluation method consists of measuring the static contact angle of water droplets. After dropping 4 μL of distilled water (20° C.) onto the sheet, the static contact angle 1 second after contact is measured with an automated contact angle meter (such as the "DM-301" manufactured by Kyowa Interface Science Co., Ltd.). At this time, a smaller static contact angle can be said to indicate greater hydrophilicity while a larger static contact angle can be said to indicate greater hydrophobicity. Another example is a method consisting of measuring the amount of time required for water droplets to be absorbed. In this method, 4 μL of distilled water (20° C.) are dropped onto the sheet followed by measuring the amount of time required for a water droplet to be absorbed. A longer amount of time required for the water droplet to be absorbed is judged to indicate greater hydrophobicity.

Another characteristic of the fine cellulose fiber sheet of the present embodiment in that the sheet is precisely controlled to a desired air permeability resistance. For example, in order for the sheet to preferably function as a filter, it is important for a cellulose non-woven fabric to have a fine network structure and a fixed air permeability. It is necessary for air permeability resistance to be within a suitable range for the reasons described above. If air permeability resistance is within the range of 1 sec/100 ml to 2000 sec/100 ml, and preferably within the range of 20 sec/100 ml to 1000 sec/100 ml, various functions as a functional filter asserted in the present invention can be preferably realized. Here, it is difficult to produce a functional filter having air permeability resistance of less than 1 sec/100 ml due to the fineness of the network, while that having air permeability resistance of greater than 2000 sec/100 ml exhibits decreased porosity and causes air resistance to increase, resulting in a material that lacks the inherent functions of a functional filter, which is also undesirable.

On the other hand, in the case of having considered use as a gas permeable membrane or gas barrier membrane, it is important for air permeability to be low. The air permeability resistance thereof is conversely preferably 1000 sec/100 ml or more. If air permeability resistance is 1000 sec/100 ml or less, air permeability becomes high making it difficult to use the membrane as a barrier membrane. Due to the nature of a gas barrier membrane, the sheet per se is preferably as dense as possible and air permeability resistance may be 1,000,000 sec/100 ml or more.

Control of this air permeability resistance can be changed depending on selection of the fiber diameter of the fine cellulose fiber used or the mixing ratio of a plurality of types of fine cellulose fibers having different fiber diameters. Fibers having a smaller fiber diameter allow the deposition of a denser film. However, air permeability resistance is changed considerably according to the selected type and added amount of the blocked polyisocyanate.

Air permeability resistance refers to the result of measuring with an Oken type air permeability tester (Model EG01, Asahi Seiko Co., Ltd.). Measurement consists of measuring at 10 different locations on a single sample sheet and determining the average thereof. Furthermore, air permeability can be measured over a range of 1 sec/100 ml to 1,000,000 sec/100 ml with this measurement method. In addition, samples having air permeability resistance of 100 sec/100 ml or less are measured by measuring air passage time of 100 ml of air using a Gurley-type densometer (Model G-B2C, Toyo Seiki Co., Ltd.) followed by determining the average value of 10 locations.

The fine cellulose fiber sheet of the present embodiment can be formed not only by a papermaking method, but also by a coating method. In order to form the sheet by a coating method in particular, it is more suitable to produce a multilayer sheet obtained by laminating layers composed of fine cellulose fibers on a base material rather than producing a single layer sheet. Furthermore, in order to form the fine cellulose fiber sheet of the present invention by a coating method, a dispersion obtained by mixing a water-dispersed blocked polyisocyanate in an aqueous dispersion of fine cellulose fibers in the same manner as the papermaking method described below is used as a coating liquid. Namely, in terms of the previously described post-processing method and internal addition method, the coating method corresponds to an internal addition method. However, the sheet of the present invention can be more preferably produced by a papermaking method. The sheet of the present invention has the advantage of superior papermaking ability when produced by a papermaking method. Superior papermaking ability as referred to herein refers to short drainage time. Differing from ordinary pulp slurries, the drainage time of the fine cellulose fibers of the present invention having a high degree of fineness is extremely long. This tendency is particularly remarkable the greater the degree of fineness. Thus, in the case of considering industrial production, it is important for drainage time to be appropriately short. More specifically, industrial production by continuous papermaking becomes difficult unless drainage time is 60 seconds or less. Drainage time is preferably 30 seconds or less and more preferably 10 seconds or less.

Drainage time is evaluated in the following manner. A papermaking slurry adjusted based on a cellulose sheet having a basis weight of 10 g/m² is placed in a batch-type papermaking machine (automated angle-type sheet machine, 25 cm×25 cm, 80 mesh, Kumagai Riki Kogyo Co., Ltd.) loaded with a blended PET/nylon plain weave fabric (NT20, water permeability at 25° C. under atmospheric pressure: 0.03 ml/cm²·s, capable of filtering off 99% or more of fine cellulose fibers by filtering at 25° C. under atmospheric pressure, Shikishima Canvas Co., Ltd.), and papermaking (dehydration) is subsequently carried out at a degree of vacuum of 4 KPa relative to atmospheric pressure. The amount of time required for dehydration at this time is measured as drainage time.

The fine cellulose fiber sheet of the present embodiment may also contain at least one type of functionalization agent selected from the group consisting of a water-repellent processing agent or water-repellent oil processing agent, water-soluble polymer, antimicrobial polymer, thermoplastic resin, thermosetting resin and photocurable resin. The solid content weight ratio of the functionalization agent is preferably within the range of 0.1% by weight to 100% by weight based on the weight of the fine cellulose fibers. If the solid content weight ratio is 0.1% by weight or less, the amount of functionalization agent is low relative to the entire fine cellulose fiber sheet, thereby preventing the function of the functionalization from being demonstrated. On the other hand, if the solid content weight ratio is 100% by weight or more, the amount of functionalization agent becomes excessive and it becomes difficult to immobilize the functionalization agent, thereby making this undesirable.

Examples of water-repellent processing agents or water-repellent oil processing agents contained in the fine cellulose fiber sheet include various types of organic-based resins containing fluorine. Polymers of unsaturated monomers containing a perfluoroalkyl group, such as acrylic acid esters, methacrylic acid esters, alkyl acrylamides, alkyl vinyl ethers or vinyl alkyl ketones, or polymers of the aforementioned perfluoroalkyl group-containing unsaturated monomers and unsaturated monomers not containing a perfluoroalkyl group, such as acrylic acid, acrylic acid esters, methacrylic acid, methacrylic acid esters, vinyl chlorides, acrylonitrile, maleic acid esters or polyoxyethylene group-containing unsaturated monomers, are particularly preferable. In addition, examples of water-repellent processing agents or water-repellent oil processing agents not containing a fluorine-based compound include silicone-based compounds such as methyl hydrogen polysiloxane, dimethylsiloxane or reactive (OH group-terminated) dimethylpolysiloxane, and wax-based compounds including ordinary wax as well as synthetic paraffin wax and paraffin wax. Furthermore, although there are numerous types of synthetic paraffin such as those having a low melting point and those having a high melting point, paraffin wax having a high melting point is preferable. In addition, modification products obtained by combining an acrylic acid ester-based polymer with paraffin can also be used to demonstrate desired actions and effects. In addition, other examples include wax-zirconium-based compounds, namely compounds obtained by reacting the aforementioned wax-based compounds with a zirconium-based compound, specific examples of which include zirconium acetate, zirconium hydrochloride, zirconium nitrate and basic zirconium obtained with potassium hydroxide and the like, alkylene urea compounds such as octadecylethylene urea and modification products thereof, and higher fatty acid amide derivatives such as aliphatic amide-based compounds such as N-methylol stearyl amide or modification products thereof. These may be used alone or two or more types may be contained in combination.

A fine cellulose fiber sheet processed with water-repellent oil can be used, for example, as a moisture-permeable waterproof film. Since the sheet per se is made of cellulose, absorption of water per se does not occur due to water-repellent processing despite having superior moisture absorption. This type of moisture-permeable waterproof film can be used in outdoor wear such as raincoats or in separator membranes for membrane distillation. In addition, it can also be applied as an oil-water separation membrane by utilizing its water repellency and oil repellency.

Moisture permeability (g/m²·24 h) can be measured by measuring moisture permeability per 24 hours in accordance with method B-1 described in JIS L1099. Moisture permeability is preferably 10,000 g/m²·24 h or more in terms of being suitable for ordinary clothing such as raincoats. In addition, water repellency can be measured according to moisture resistance test method B (high water pressure method) of JIS L1092-1998. Water bearing pressure is preferably 100 kPa or more in terms of being suitable for ordinary clothing such as raincoats. In addition, water repellency as determined according to the rain-shower test using the spray method of JIS L1092, sliding angle in the static contact angle or dynamic contact angle using water droplets (surface tension: 72 mN/m), and measurement of hysteresis representing the difference between advancing contact angle and receding contact angle may be evaluated as indicators of water repellency. Furthermore, oil repellency can also be evaluated by measuring the aforementioned static contact angle and dynamic contact angle using n-hexadecane droplets (surface tension: 27 nM/m).

The water-soluble polymer contained may be cationic, anionic, amphoteric or nonionic.

Cationic polymers consist of polymers having a primary amino group, secondary amino group, tertiary amino group, quaternary ammonium group, pyridinium, imidazolium or quaternary pyrrolidone, and examples thereof include water-soluble cationic polymers such as cationic starch, cationic polyacrylamide, polyvinylamine, polydiallyl-dimethyl ammonium chloride, polyamidoamine epichlorohydrin, polyethyleneimine and chitosan.

Anionic polymers consist of polymers having an anionic group such as a carboxyl group, sulfonate group or phosphate group, and examples thereof include carboxymethyl cellulose, polyacrylic acid, anionic polyacrylamide, starch urea phosphate, succinic acid-modified starch and sodium polystyrene sulfonate.

Examples of amphoteric polymers include amphoteric water-soluble polymers containing both anionic monomer units and cationic monomer units in the molecular chain backbone. Examples thereof include diallylamine hydrochloride-maleic acid copolymer and amphoteric polyacrylamide.

Examples of nonionic polymers include polyethylene glycol, hydroxypropyl methyl cellulose and polyvinyl alcohol.

Immobilizing these water-soluble polymers makes it possible to freely control the surface zeta potential of a sheet. By controlling surface zeta potential, substances can be adsorbed by electrostatic interaction or adsorption can be intentionally inhibited. For example, when the sheet surface has a cationic charge, anionic substance are adsorbed while it becomes difficult to adsorb cationic substances. In addition, in the case the sheet surface has an anionic charge, cationic substances are adsorbed while it becomes difficult to adsorb anionic substances. As a result of having this characteristic, a target substance can be captured utilizing adsorption by electrostatic interaction even with a filter having a smaller pore diameter than the substance to be filtered when using as an adsorption filter for water treatment, for example. In addition, since there are many cases in which microparticles responsible for fouling of water treatment membranes are anionic, making the sheet anionic makes it possible to prevent adsorption of microparticles and prolong membrane life.

The adsorption capacity of a fine cellulose fiber sheet immobilized with a water-soluble polymer by using electrostatic interaction can be evaluated using the method indicated below. In the case of desiring to evaluate the adsorption capacity of an anionic substance, for example, the fine cellulose fiber sheet of the present invention is used as a filtering material, and the entire amount of an aqueous solution containing an anionic pigment in the form of Orange II having a concentration of 1 ppm (Kanto Chemical Co., Ltd.) is filtered at a differential pressure of 100 kPa and effective filtration area of 3.5 cm². The concentration C (ppm) of the filtrate is measured and the removal rate (%) of the anionic pigment is calculated according to the equation indicated below.

Anionic component removal rate (%)=(1−C)×100

Concentration C (ppm) of the filtrate containing Orange II can be measured by using an ultraviolet-visible spectrophotometer (V-650, Jasco Corp.) and preparing a calibration curve of known concentrations of Orange II (wavelength: 485 nm). The absorption capacity of a cationic substance can be measured in the same manner as described above by using methylene blue (wavelength: 665 nm) instead of Orange II.

The surface zeta potential of the fine cellulose fiber sheet of the present embodiment is required to be −100 mV to +100 mV over a pH range of 1 to 14 corresponding to the objective. If the pH is below 1 or above 14, since the fine cellulose fiber sheet is easily subjected to chemical modification by acid or base, it becomes difficult to retain the shape of the sheet. In addition, there are typically no substances having a zeta potential of lower than −100 mV or higher than +100 mV.

Zeta potential can be measured with an electrophoretic light scattering photometer. For example, zeta potential can be measured by rinsing the sheet with ultrapure water, placing the sheet in a plate sample cell so that surfaces of the fine cellulose fibers contact a monitoring particle solution (polystyrene latex), and measuring with an electrophoretic light scattering photometer (Zetasizer Nano ZS, Malvern Instruments Ltd.). In addition, zeta potential can be measured at a prescribed pH by adjusting the pH of the monitoring particle solution.

Examples of antimicrobial polymers include polyhexamethylene biguanide hydrochloride, chlorhexidine, 2-acrylamido-2-methylpropanesulfonate copolymer, polymethacrylic acid, mixtures of polyacrylic acid and zinc sulfate, quaternary ammonium salt compounds of copolymers of phosphate ester monomers, dicyanamide, polyalkylenepolyamine ammonium polycondensates, reaction products of partially deacetylated compounds of (poly-β-1,4)-N-acetyl-D-glucosamine and hexamethylene-bis(3-chloro-2-hydroxypropyldimethylammonium chloride), copper-crosslinked acrylonitrile-acrylic acid copolymers, acrylamide-diallylamine hydrochloride copolymers, methacrylate copolymers, hydroxypropyl chitosan, crosslinked chitosan, chitosan organic salts, chitosan fine powder (polyglucosamine), chitin fibers and N-acetyl-D-glucosamine. These antimicrobial polymers can be immobilized on a sheet surface by blocked polyisocyanate to provide, for example, antimicrobial clothing fabric (sheets) having superior laundering resistance.

Evaluation of antimicrobial activity can be carried out in accordance with the antimicrobial fabric test (unified test method) enacted in JIS-1902-1998. More specifically, 2 g of sample are preliminarily placed in the bottom of a closed container, 0.2 ml of a microbial suspension of preliminarily cultured *Staphylococcus aureus* (test species: AATCC-6538P) diluted by a factor of 1/50 with broth is disseminated on the sample, and after allowing to stand undisturbed for 18 hours in an incubator at 37° C., 20 mL of SCDLP medium are added following by shaking well to rinse off the bacteria. The bacteria are then placed on ordinary agar medium and counted after 24 hours, and antimicrobial activity is evaluated by comparing with the bacterial count obtained from an unprocessed sample fabric treated in the same manner:

$$D=(Ma-Mb)-(Mc-Md)$$

wherein,

Ma: Log of viable bacteria count after culturing unprocessed sample for 18 hours;
(average of 3 specimens)

Mb: Log of viable bacteria count immediately after inoculating unprocessed sample;
(average of 3 specimens)

Mc: Log of viable bacterial count after culturing processed fabric for 18 hours;

Md: Log of viable bacterial count immediately after inoculating processed fabric; and D: Viable bacteria activity value When the viable bacterial activity value D is equal to or greater than 2.2, the fabric is judged to have antimicrobial activity. Thus, the fine cellulose fiber sheet also preferably has a viable bacteria activity value D of 2.2 or more.

Examples of thermoplastic resins include styrene-based resins, acrylic resins, aromatic polycarbonate-based resins, aliphatic polycarbonate resins, aromatic polyester-based resins, aliphatic polyester-based resins, aliphatic polyolefin-based resins, cyclic olefin-based resins, polyamide-based resins, polyphenylene ether-based resins, thermoplastic polyimide-based resins, polyacetal-based resins, polysulfone-based resins and amorphous fluorine-based resins. The number average molecular weight of these thermoplastic resins is typically 1,000 or more, preferably 5,000 to 5,000,000, and even more preferably 10,000 to 1,000,000. These thermoplastic resins may be contained alone or two or more types may be contained. In the case of containing two or more types of thermoplastic resins, resin refractive index can be adjusted according to the fraction at which they are contained, thereby making this preferable. For example, containing poly(methyl methacrylate) (refractive index: 1.49) and acrylonitrile styrene (acrylonitrile content: approx. 21%, refractive index: 1.57) at a ratio of 50:50 allows the obtaining of a resin having a refractive index of 1.53.

There are no particular limitations on thermosetting resins, and specific examples thereof include epoxy resin, thermosetting-type modified polyphenylene ether resin, thermosetting-type polyimide resin, urea resin, allyl resin, silicone resin, benzoxazine resin, phenol resin, unsaturated polyester resin, bismaleimide-triazine resin, alkyd resin, furan resin, melamine resin, polyurethane resin, aniline resin, other industrial resins and resins obtained by mixing two or more types thereof. Among these, epoxy resin, allyl resin, unsaturated polyester resin, vinyl ester resin and thermosetting-type polyimide resin are preferable in the case of using as an optical material due to their transparency.

Examples of photocurable resins include epoxy resins containing a latent photocationic polymerization initiator. These thermosetting resins or photocurable resins may be contained alone or two or more types may be contained.

Furthermore, thermosetting resins and photocurable resins refers to substances that are a liquid, semi-solid or solid at normal temperatures and have a comparatively low molecular weight that enables them to demonstrate fluidity at normal temperatures or when heated. These resins can be used as insoluble, infusible resins obtained by a network-like three-dimensional structure while increasing molecular weight by undergoing a curing reaction or crosslinking reaction due to the action of a curing agent, catalyst, heat or light. In addition, a cured resin refers to a resin obtained by curing the aforementioned thermosetting resins or photocurable resins.

There are no particular limitations on the curing agent or curing catalyst provided they are used to cure thermosetting resins and photocurable resins. Specific examples of curing agents include polyfunctional amines, polyamides, acid anhydrides and phenol resins, specific examples of curing catalysts include imidazole, and these may be contained in the present invention alone or as a mixture of two or more types thereof.

In a fine cellulose fiber sheet, the aforementioned functionalization agent preferably bonds with the blocked polyisocyanate. As a result of the blocked polyisocyanate chemically bonding with the fine cellulose fibers in addition to bonding with the functionalization agent, the functionalization agent can be immobilized within and/or on the surface of the fine cellulose fiber layer. For example, in the case of using the sheet as a water filter, elution of the functionalization agent can be prevented by immobilizing the functionalization agent. Thus, functions derived from the functionalization agent can be sustained even after using in water for a long period of time.

The following three methods can be used to verify whether or not a functionalization agent is immobilized. These methods consist of immersing a sheet immobilized with a functionalization agent in a solvent that easily dissolves the functionalization agent or enables it to swell easily, followed by i) evaluating to what degree the functionality thereof is maintained, ii) analyzing the amount of the decrease in the functionalization agent in the sheet, and iii) quantifying the amount of functionalization agent eluted into the solvent. For example, if the sheet is immobilized with a fluorine-based water and oil repellent, the aforementioned water repellency and oil repellency tests are carried out on samples before and after immersion following by evaluating variations thereof. In addition, immobilization of a functionalization agent can also be evaluated by analyzing changes in the amount of fluorine derived from the fluorine-based water and oil repellent contained in the sheet following immersion by combustion ion chromatography. Furthermore, the analysis method is not limited to combustion ion chromatography, but rather a method may be selected that facilitates analysis according to the type of functionalization agent to be analyzed, examples of which include solution NMR, solid-state MAS-NMR, ICP, liquid chromatography, gas chromatography and TOF-SIMS.

Since a laminated structure obtained by laminating the fine cellulose fiber sheet of the present embodiment with a sheet composed of an organic polymer (to be abbreviated as an organic polymer sheet) is strong as a result of having enhanced tensile strength and the like, handling as a sheet is improved. This is particularly effective in applications involving contact with a liquid such as water treatment filters, separation membranes or cell culture sheets.

There are no particular limitations on the organic polymer sheet, and it is sufficient to select a material corresponding to the required performance of the target laminated structure with respect to shape, hardness, mechanical properties, thermal properties, durability, water permeability, air permeability resistance or filterability and the like, as well as the application thereof.

There are no particular limitations on the polymer composition, and examples thereof include polyethylene, polypropylene, ethylene-propylene copolymer, polyvinyl chloride, polyvinylidene chloride, polyvinyl acetate, ethylene-vinyl acetate copolymer, polyvinyl alcohol, polyacetal, polyvinylidene fluoride and other fluorine resins, polyethylene terephthalate, polybutylene terephthalate, polyethylene naphthalate, polystyrene, polyacrylonitrile, styrene-acrylonitrile copolymer, ABS plastic, polyphenylene ether (PPE) resin, polyimide, polyamidoimide, polymethacrylic acid, polyacrylic acid, polycarbonate, polyphenylene sulfide, polysulfone, polyethersulfone, polyethernitrile, polyetherketone, polyketone, liquid crystal polymers, silicone resin, ionomers, cellulose, cellulose derivatives, cellulose acetate, nitrocellulose, styrene-butadiene or styrene-isoprene block copolymer, styrene-based thermoplastic elastomers, olefin-based thermoplastic elastomers, vinyl chloride-based thermoplastic elastomers, polyester-based thermoplastic elastomers, polyurethane-based thermoplastic elastomers, polyamide-based thermoplastic elastomers, epoxy resin, polyimide resin, phenol resin, polyurethane resin, polyimidosilicone resin, thermosetting-type polyphenylene ether resin, modified PPE resin, natural rubber, butadiene rubber, isoprene rubber, styrene-butadiene copolymer rubber, nitrile rubber, chloroprene rubber, ethylene-propylene rubber, chlorinated polyethylene, chlorosulfonated polyethylene, butyl rubber and halogenated butyl rubber, fluorine rubber, urethane rubber and silicone rubber.

The surface of the aforementioned organic polymer sheet may be subjected to surface modification by corona discharge treatment or plasma treatment and the like.

In the laminated structure of the present embodiment, there are no particular limitations on the structure of the organic polymer sheet. However, from the viewpoint of producing according to a papermaking method by filtering fine cellulose fibers, and from the viewpoint of using for the purpose of substance filtration such as in the case of a water treatment filter, a porous sheet is more preferable. Examples of porous sheets include woven fabric, knit fabric, mesh, long fiber non-woven fabric and short fiber non-woven fabric composed of organic polymer fibers, and polymer microporous membrane or films produced by phase separation or stretching of a resin. Among these, from the viewpoint of imparting a function to the sheet, and from the viewpoint of papermaking ability during production as well as sheet cost or flexibility and the like, a sheet composed of organic polymer fibers (to also be referred to as a polymer fiber sheet) is more preferable.

In the case of considering use as a water treatment filter or separation membrane, a number average fiber diameter of the organic polymer fibers as number average fiber diameter is preferably 0.5 μm to 30 μm in order to improve strength and maintain flexibility of the fine cellulose fiber sheet as well as for the purpose of membrane quality uniformity. In addition, by simultaneously making the number average fiber diameter of the organic polymer fibers to be within this range, the organic polymer fiber layer forms pores of several μm to several tens of μm, enabling it to also act as a filtering material for coarse particles. The weight ratio of organic polymer fibers with respect to the fine cellulose fiber sheet is preferably 100% by weight to 3000% by weight, and by making the weight ratio to be 100% by weight or more, overall strength of a sheet containing a fine cellulose fiber layer is improved. On the other hand, if the weight ratio of organic polymer fibers exceeds 3000% by weight, characteristics of the fine cellulose fibers (such as high adsorption performance attributable to the high specific surface area thereof) are inhibited. Thus, the fiber diameter of the organic polymer fibers is preferably 1 μm to 25 μm and more preferably 1.5 μm to 20 μm, while the weight ratio of the organic polymer fiber layer is preferably 150% by weight to 2500% by weight and more preferably 200% by weight to 2000% by weight.

Organic polymer fibers refer to at least one type selected from the group consisting of polyamide fibers such as Nylon 6 or Nylon 6,6, polyester fibers such as polyethylene terephthalate, polytrimethylene terephthalate or polybutylene terephthalate, polyethylene fibers, polypropylene fibers, natural cellulose fibers such as wood pulp or cotton linter, regenerated cellulose fibers such as viscose rayon or cuprammonium rayon, and refined cellulose fibers such as lyocell or tencel. The layer composed of the aforementioned organic polymer fibers may be a long fiber sheet or short fiber sheet, and in the case of a long fiber sheet, may be a non-woven fabric, woven fabric, knit fabric or mesh.

In addition, the surface of the aforementioned polymer fiber sheet may be subjected to corona discharge treatment or plasma treatment in order to improve adhesion. Fine cellulose fibers may be incorporated in the aforementioned organic polymer fiber layer in the direction of thickness for the purpose of preventing separation of the fine cellulose fiber layer and organic polymer fiber layer and slippage from the fine cellulose fiber sheet.

The structure of the laminated structure of the present embodiment may be a two-layer structure in which the fine cellulose fiber sheet is laminated on the organic polymer sheet, or a three-layer structure in which the cellulose sheet is arranged on the front and back of the organic polymer sheet. In addition, the fine cellulose fiber sheet may be arranged on one side or both the front and back sides of a multilayer sheet composed of different organic polymers, or an organic polymer sheet may be further arranged on one side or both the front and back sides of these sheets having a laminated structure. The weight ratio of the organic polymer sheet based on sheet weight is determined based on the total weight of the organic polymer sheet used.

The aforementioned laminated structure of the fine cellulose fiber sheet and organic polymer sheet is preferably chemically crosslinked by a blocked polyisocyanate. Chemical crosslinking agents maintain the multilayered structure with, for example, urethane bonds formed by a reaction with hydroxyl groups, urea bonds formed by a reaction with amino groups or amidourea bonds formed by reacting with carboxyl groups. In the case of the absence of chemical crosslinking, the laminated structure is maintained by weak bonds in the manner of hydrogen bonds or ionic bonds formed between the fine cellulose fibers and organic polymer. Consequently, since the resulting structure is susceptible to water and easily undergoes separation in water, its application and deployment are severely limited. Thus, separation of the fine cellulose fiber sheet and organic polymer sheet can be prevented by crosslinking both sheets with the blocked polyisocyanate.

An organic polymer sheet that is preferable in terms of being crosslinked by the blocked polyisocyanate is a sheet that has a large number of functional groups (such as hydroxyl groups, amino groups, carboxyl groups or thiol groups) having active hydrogens that highly react with isocyanate groups on the surface of the organic polymer sheet. The reason for this is that both sheets are strongly chemically crosslinked by a large number of covalent bonds due to the presence of a large number of the functional groups on the sheet surface. Preferable examples of organic polymer sheets include those composed of cellulose, nylon, polyvinyl alcohol or polycarboxylic acid fibers. In addition, even an organic polymer sheet not having those functional groups in the manner of polyethylene, polypropylene or polyethylene terephthalate sheets can be introduced with those functional groups by subjecting to corona discharge treatment or plasma treatment and the like, and can be chemically crosslinked by the blocked polyisocyanate.

As a result of the laminated structure being chemically crosslinked as described above, it can be used in water filters, separation membranes and cell culture sheets that are contact with water for extended periods of time, or in gas barrier membranes or total heat exchanger sheets and the like require high dimensional stability when highly hydrated. In addition, since crosslinking also improves tensile strength and tensile elongation even when dry, handling of the laminated structure per se becomes easy. Thus, this is also effective in applications in applications where there is no contact with water such as air filters.

The laminated structure of the present embodiment is able to improve water vapor permeability of a sheet by being subjected to hydrophilic treatment. A sheet having improved permeability is preferable for use as, for example, a total heat exchanger sheet. A total heat exchanger sheet refers to a member used in a total heat exchanger that reduces air-conditioning energy by ventilation. The sheet is superior in terms of the transfer of sensible heat and the transfer of latent heat by allowing the passage of moisture without mixing two types of air having different temperature and humidity. Thus, this sheet is required to provide three functions consisting of: i) high air permeability resistance (denseness) that does allow the passage of air, ii) membrane thinness that allows the efficient transfer of sensible heat, and iii) high moisture permeability that allows the efficient permeation of moisture. In general, the permeation of not only air, but also moisture decreases if air permeability resistance is increased. In response to this, carrying out hydrophilic treatment allows the obtaining of a sheet having superior moisture permeability despite having high gas barrier properties.

Means used to carry out hydrophilic treatment consist of a method in which a high degree of hydrophilicity is imparted to the surface and/or interior of a fine cellulose fiber layer by internal addition, and a method in which a hydrophilic compound is introduced into the surface layer of the laminated structure by post-processing.

Internal addition can be achieved by a method in which the previously described water-soluble polymer is immobilized during immobilization of the previously described functionalization agent.

Examples of post-processing methods include a method consisting of coating or spraying a solution of dispersion of a highly hydrophilic compound onto the laminated structure, and a method consisting of immersing the laminated structure in a solution of a hydrophilic compound followed by drying.

Examples of hydrophilic compounds able to be used in post-processing include inorganic acid salts, organic acid salts, inorganic fillers, polyvalent alcohols, ureas and moisture absorbent (water absorbent) polymers (water-soluble polymers and hydrophilic polymers having the ability to form a hydrogel), examples of inorganic salts include lithium chloride, calcium chloride and magnesium chloride, examples of organic salts include sodium lactate, calcium lactate and sodium pyrrolidone carboxylate, examples of inorganic fillers include aluminum hydroxide, calcium carbonate, aluminum silicate, magnesium silicate, talc, clay, zeolite, diatomaceous earth, sepiolite, silica gel and activated charcoal, examples of polyvalent alcohols include glycerin, ethylene glycol, triethylene glycol and polyglycerin, examples of ureas include urea and hydroxyethylurea, and examples of moisture absorbent (water absorbent) polymers include polyaspartic acid, polyacrylic acid, polyglutamic acid, polylysine, alginic acid, carboxymethyl cellulose, carboxyethyl cellulose, hydroxyalkyl cellulose and salts or crosslinked products thereof, carrageenan, pectin, gellan gum, agar, xanthan gum, hyaluronic acid, gua gum, gum arabic, starch and crosslinked products thereof, polyethylene glycol, polypropylene glycol, collagen, acrylonitrile-based polymer saponification products, starch-acrylonitrile graft copolymers, acrylate-acrylamide copolymers, polyvinyl alcohol-maleic anhydride copolymers, polysaccharide-acrylate graft autocrosslinked products and other hygroscopic agents, and the types and adhered amounts thereof are selected and used corresponding to the target degree of moisture absorption. Furthermore, the aforementioned inorganic filler refers to an inorganic mineral or inorganic salt and the like that is used for the purpose of moisture absorption in addition to use as an extender or bulking agent and the like. There are cases in which it is effective to combine the aforementioned water-soluble polymer with inorganic salts and organic salts for the purpose of immobilizing the hygroscopic agent (so as to prevent migration of the hygroscopic agent at high humidity).

In the laminated structure of the present embodiment, the blocked polyisocyanate Is used for the purpose of imparting water resistance to the sheet. More specifically, the blocked polyisocyanate prevents collapse of the sheet when used in highly wet environments or in environments where there is condensation of moisture. In addition to the aforementioned blocked polyisocyanate and hydrophilic compounds, flame retardants and other optional additives may be contained within a range that does not impair the moisture permeability or air permeability resistance of the laminated structure of the present invention. The contained amounts of the aforementioned blocked polyisocyanate, hydrophilic compound and other additives is preferably held to 50% by weight or less of the total weight of the sheet, more preferably to 40% by weight or less and even more preferably to 30% by weight or less. If within these ranges, the laminated structure of the present invention can be provided that is provided with both high gas barrier properties and high moisture permeability. On the other hand, since additives have high levels of activity as chemical substances in exchange for demonstrating various target effects, if the total content thereof exceeds 50% by weight, the durability of the sheet is significantly impaired, thereby making this undesirable.

In the case of using for the purpose of a total heat exchanger sheet, the laminated structure of the present embodiment preferably has air permeability resistance (as measured according to pulp and paper testing methods of the Japan Technical Association of the Pulp and Paper Industry (TAPPI)) of 1,000 sec/100 ml or more. If air permeability resistance is less than 1,000 sec/100 ml, since the resulting sheet is permeable to both moisture and air, it is unable to demonstrate the function of ventilation. In order to demonstrate the function of heat exchange, air permeability resistance is preferably 3,000 sec/100 ml or more, and in the case of using as a total heat exchanger sheet, preferably 4,000 sec/100 ml or more. Although the upper limit of air permeability resistance is preferably as high as possible (large as possible), it is preferably 10,000,000 sec/100 ml or lower, which is the detection limit of measuring instruments.

When using for the purpose of a total heat exchanger sheet, moisture permeability of the laminated structure of the present embodiment (as measured in accordance with method A-1 of JIS L-1099) is preferably 5000 $g/m^2 \cdot 24$ h, more preferably 7000 $g/m^2 \cdot 24$ h and even more preferably 8000 $g/m^2 \cdot 24$ h. Moisture permeability is preferably as high as possible when using as a total heat exchanger sheet. In addition to the addition of a hydrophilic compound as previously described, reducing the thickness of the fine cellulose fiber layer that resists permeation of water vapor is also effective as a method for improving moisture permeability.

When using for the purpose of a total heat exchanger sheet, the laminated structure of the present embodiment has a comparatively high level of thermal conductivity of 0.0100 $W/(m \cdot K)$ to 0.1000 $W/(m \cdot K)$. Thermal conductivity is substantially governed by the dense fine cellulose fiber layer that is resistant to the flow of air. Thus, thermal conductivity of the laminated structure can be improved by reducing the thickness of this layer. Namely, this enables the laminated structure to realize a sensible heat exchange rate.

In the case of using for the purpose of a total heat exchanger sheet, a thin total heat exchanger sheet of the present embodiment is used preferably based on the requirements of compact size and thermal conductivity of the total heat exchange elements, and the total average thickness thereof is 10 µm to 200 µm, preferably 10 µm to 120 µm and more preferably 10 µm to 70 µm. It is technically difficult to produce a sheet having an average thickness of less than 10 µm, while a sheet having an average thickness of greater than 20 µm results in a considerable decrease in thermal conductivity, thereby making this undesirable.

On the basis of the above, the laminated structure of the present embodiment has high air permeability resistance, high moisture permeability and comparatively high thermal conductivity for the purpose of using as a total heat exchanger sheet. This sheet is preferably used as a partition that divides intake air and exhaust air in a total heat exchange element (laminate cartridge referred to as an element) used in static-type total heat exchangers, and is able to contribute to a high rate of energy conversion.

The aforementioned total heat exchange element forms a total heat exchanger by combining with a supply fan and an exhaust fan. A total heat exchanger operates in a system like that indicated below. Supply air such as outside air is drawn into the total heat exchange element by the supply fan where it contacts a total heat exchanger sheet incorporated within the total heat exchange element. On the other hand, exhaust air such as interior air is also drawn into the total heat exchange element by the exhaust fan where it also contacts the total heat exchanger sheet. The supply air and exhaust air, which have made contact through the total heat exchanger sheet, respectively undergo heat exchange corresponding to their temperature and humidity. Following heat exchange, the supply air is blown into the supply fan and supplied to a room, for example. On the other hand, exhaust air that has undergone heat exchange is blown into the exhaust fan and discharged to the outside, for example.

At this time, heat can be efficiently exchanged between the supply air and exhaust air if the total heat exchanger sheet has superior moisture permeability performance and thermal conductivity. As a result, carbon dioxide, containing highly concentrated, volatile organic compounds, in a building can be discharged and fresh, outside air can be supplied while inhibiting the release or warmth or cold in the building.

Furthermore, the laminated structure of the present invention having high moisture permeability, high air permeability resistance and comparatively high thermal conductivity can also be applied to applications other than a total heat exchanger sheet. Examples of such applications include, but are not limited to, water treatment membranes in the manner of membrane distillation and clothing materials requiring high water bearing pressure and water vapor permeability.

Although the following provides an explanation of an example of a method for producing the fine cellulose fiber sheet of the present invention, the production method used is not particularly limited thereto.

The fine cellulose fiber sheet of the present embodiment is produced by either a papermaking method or coating method. In the case of using a papermaking method, the production method consists of (1) a fine cellulose fiber production step carried out by reducing the fineness of the cellulose fibers, (2) a preparation step for preparing a papermaking slurry of the fine cellulose fibers, (3) a papermaking step for forming wet paper by filtering the papermaking slurry on a porous base material, (4) a drying step for obtaining a dry sheet by drying the wet paper, and (5) a heat treatment step for promoting the formation of chemical bonds by a blocked polyisocyanate by heat-treating the dry sheet. In addition, in the case of using a coating method, a coating slurry, prepared using the same steps as the aforementioned steps (1) and (2), is coated and dried on an organic polymer sheet, and the formation of chemical bonds by heat treatment is promoted in the same manner as the aforementioned step (5). Various methods such as spray coating, gravure coating or dip coating can be selected for the coating method in the case of coating.

The following provides an explanation of a method used to prepare a papermaking slurry or coating slurry composed of fine cellulose fibers of the present invention, and a method used to form a fine cellulose fiber layer by a papermaking method.

So-called wood pulp, such as softwood pulp or hardwood pulp, and non-wood pulp can be used as raw materials when producing the fine cellulose fibers. Examples of non-wood pulp include cotton-derived pulp, including cotton linter pulp, hemp-derived pulp, bagasse-derived pulp, kenaf-derived pulp, bamboo-derived pulp and straw-derived pulp. Cotton-derived pulp, hemp-derived pulp, bagasse-derived pulp, kenaf-derived pulp, bamboo-derived pulp and straw-derived pulp respectively refer to refined pulp obtained by going through refining and bleaching steps such as delignification by carrying out digestive treatment on raw materials such as cotton lint, cotton linter, manila hemp (which is frequently of Ecuador or Philippine origin), zaisal, bagasse, kenaf, bamboo or straw. In addition, refined products of algae-derived cellulose and sea squirt cellulose can also be used as raw materials of fine cellulose fibers. Moreover, cut yarn of regenerated cellulose fibers and cut yarn of cellulose derivative fibers can also be used as raw materials, and cut yarn of regenerated cellulose obtained by electrospinning and cut yarn of fine threads of cellulose derivatives can be used as raw materials of fine cellulose fibers or as fine cellulose fibers per se.

Next, a description is provided of a method for reducing the diameter of cellulose fibers. Reduction of the diameter of cellulose fibers preferably goes through a pretreatment step, a beating treatment step and a diameter reduction step. In the aforementioned pretreatment step, it is effective to put the raw material pulp into a state that facilitates diameter reduction by carrying out autoclaving treatment, enzyme treatment or a combination thereof while impregnating with water at a temperature of 100° C. to 150° C. Since this pretreatment is also effective for not only reducing the load of fiber reduction treatment, but also causing impurities such as lignin or hemicellulose present on the surface and gaps of microfibrils composing the cellulose fibers to be discharged into the aqueous phase, thereby enhancing the α-cellulose purity of the diameter-reduced fibers, it is very effective for improving the heat resistance of a fine cellulose fiber nonwoven fabric.

In the beating treatment step, the raw material pulp is dispersed in water so a solid content concentration of 0.5% by weight to 4% by weight, preferably 0.8% by weight to 3% by weight and more preferably 1.0% by weight to 2.5% by weight, and a high degree of fibrillation is promoted with a beating device in the manner of a beater or disk refiner (double disk refiner). In the case of using a disk refiner, since beating (fibrillation) proceeds to an extremely high degree if treatment is carried out by setting the clearance between the disks to be as narrow as possible (for example, 0.1 mm or less), the conditions of fiber reduction treatment using a high-pressure homogenizer and the like can be relaxed, which may be effective in some cases.

The preferable degree of beating treatment is determined in the manner described below. In a study conducted by the inventors of the present application, as beating treatment is carried out, CSF value (indicating the degree of cellulose beating and evaluated with the Canadian standard pulp freeness test method defined in JIS P 8121) was confirmed to tend to decrease over time, and after once having approached zero, again increase when beating treatment is continued, and in order to prepare the fine cellulose fibers serving as raw materials of the nonwoven fabric structure of the present embodiment, it was determined that is preferable to carry out pretreatment consisting of continuing beating treatment after the CSF value had approached zero, and then carrying out beating to a state in which the CSF value increased. In the present description, a CSF value that is in the process of decreasing from an unbeaten state is represented with *↓, while a CSF value that is demonstrating an increasing trend after having decreased to zero is represented with *↑. In the beating treatment, the CFS value is preferably at least zero and more preferably 30↑. In an aqueous dispersion prepared to this degree of beating, fibrillation proceeds to a high degree and a uniform sheet composed of fine cellulose fibers having a number average fiber diameter of 1000 nm or less is obtained. In addition, simultaneously thereto, the resulting fine cellulose fiber sheet tends to have improved tensile strength perhaps due to an increase in the number of contact sites between cellulose microfibrils. In addition, an aqueous dispersion in which beating treatment has been carried out to a high degree having a CSF value of at least zero, or a ***↑ value that increases thereafter, offers the advantages in terms of production efficiency of being able to increase uniformity and decrease clogging during subsequent fiber reduction treatment caused by a high-pressure homogenizer and the like.

In producing the fine cellulose fibers, diameter reduction is preferably carried out with a high-pressure homogenizer, ultra-high-pressure homogenizer or grinder and the like following the previously described beating treatment. The solid content concentration of the aqueous dispersion at this time is 0.5% by weight to 4% by weight, preferably 0.8% by weight to 3% by weight and more preferably 1.0% by weight to 2.5% by weight in compliance with the aforementioned beating treatment. In the case of a solid content concentration within these ranges, there is no occurrence of clogging and efficient diameter reduction treatment can be achieved.

Examples of high-pressure homogenizers used include the Model NS High-Pressure Homogenizer manufactured by Niro Soavi S.P.A. (Italy), the Lanier Type (R Model) High-Pressure Homogenizer manufactured by SMT Co., Ltd., and the High-Pressure Homogenizer manufactured by Sanwa Machinery Trading Co., Ltd., and devices other than those listed above may also be used provided they are devices that carry out diameter reduction using roughly the same mechanism as these devices. Ultra-high-pressure homogenizers refer to the Micro Fluidizer manufactured by Mizuho Industrial Co., Ltd., the Nanomizer manufactured by Yoshida Kikai Co., Ltd., and the Ultimizer manufactured by Sugino Machine Ltd., and devices other than those listed above may also be used provided they are devices that carry out diameter reduction using roughly the same mechanism as these devices. Although examples of grinder-type diameter reduction devices include the Pure Fine Mill manufactured by Kurita Machinery Mfg. Co., Ltd., and a millstone-type grinder represented by the Super Mass Colloider manufactured by Masuko Sangyo Co., Ltd., devices other than those listed above may also be used provided they are devices that carry out diameter reduction using roughly the same mechanism as these devices.

The diameter of the fine cellulose fibers can be controlled by the conditions of diameter reduction treatment with a high-pressure homogenizer and the like (device selection, operating pressure and number of passes) along with the conditions of pretreatment prior to the diameter reduction treatment (such as autoclaving treatment, enzyme treatment or beating treatment).

Moreover, cellulose-based fine fibers subjected to chemical treatment of the surface thereof and cellulose-based fine fibers in which the hydroxyl group at position 6 has been oxidized to a carboxyl group (including acid and base types) by a TEMPO oxidation catalyst can also be used as fine cellulose fibers able to be used in the present invention. In the case of the former, fine cellulose fibers in which all or a portion of the hydroxyl groups present on the surface of fine cellulose fibers have been esterified, including acetic acid esters, nitric acid esters or sulfuric acid esters, or those in which they have been etherified, including alkyl ethers represented by methyl ether, carboxy ethers represented by carboxymethyl ether, or cyanoethyl ether, for example, can be suitably prepared and used by carrying out various chemical treatment on the surface according to the specific objective. In addition, in the case of the latter, namely the preparation of fine cellulose in which the hydroxyl group at position 6 has been oxidized by a TEMPO oxidation catalyst, a fine cellulose dispersion can be obtained without necessarily requiring the use of a diameter reduction device requiring a large amount of energy in the manner of a high-pressure homogenizer. For example, as described in the literature (A. Isogai, et al., Biomacromolecules, 7, 1687-1691 (2006)), by combining a catalyst referred to as a TEMPO catalyst in the manner of a 2,2,6,6-tetramethylpiperidinooxy free radical with an alkyl halide in an aqueous dispersion of natural cellulose, adding an oxidizing agent in the manner of hypochlorous acid, and allowing the reaction to proceed for a certain amount of time, a dispersion of fine cellulose fibers can be obtained extremely easily by carrying out ordinary mixing treatment following rinsing or other purification treatment.

Furthermore, in the present invention, a sheet composed of two or more types of fine cellulose fibers can be produced by carrying out the papermaking, drying and heat treatment to be subsequently described using a dispersion obtained by mixing two or more types of the aforementioned fine cellulose fibers having different raw materials, fine cellulose fibers having different degrees of fibrillation or fine cellulose fibers subjected to chemical treatment of the surface thereof at an arbitrary ratio.

Next, a description is provided of the aforementioned step for preparing a papermaking slurry by adding various types of additives (such as an oily compound, blocked polyisocyanate or functionalization agent) to an aqueous dispersion of the fine cellulose fibers. A fine cellulose fiber concentration of preferably 0.01% by weight to 0.5% by weight, and more preferably 0.08% by weight to 0.35% by weight, of the fine cellulose fiber papermaking slurry enables to papermaking to preferably be carried out stably. If the cellulose fiber concentration in the slurry is lower than 0.01% by weight, filtration time becomes extremely long, which simultaneous to significantly lowering productivity, results in considerably poor membrane quality uniformity, thereby making this undesirable. In addition, if the fine cellulose fiber concentration is higher than 0.05% by weight, dispersion viscosity ends up increasing excessively and uniform deposition becomes difficult, thereby making this undesirable.

In terms of producing a porous fine cellulose fiber sheet, an emulsified oily compound described in the aforementioned Patent Document 1 by the inventors of the present invention may be contained in the aforementioned papermaking slurry.

More specifically, an oily compound having a boiling point range at atmospheric pressure of 50° C. to 200° C. is preferably dispersed in the papermaking slurry in the form of a emulsion at 0.15% by weight to 10% by weight. The concentration of the oily compound in the papermaking slurry is preferably 0.15% by weight to 10% by weight, more preferably 0.3% by weight to 5% by weight and even more preferably 0.5% by weight to 3% by weight. Although the fine cellulose fiber porous sheet of the present invention can be obtained even if the concentration of the oily compound exceeds 10% by weight, the amount of oily compound used in the production process becomes large, and this is accompanied by the need for safety measures and the occurrence of cost constraints, thereby making this undesirable. In addition, if the concentration of the oily compound becomes less than 0.15% by weight, it is only possible to obtain a sheet having higher air permeability resistance than a prescribed air permeability resistance range, thereby again making this undesirable.

Since the fine cellulose fiber porous sheet of the present invention cannot be obtained unless the aforementioned oily compound is removed during drying, the oily compound used is required to be able to be removed in the drying step. Thus, in the present invention, the oily compound contained as an emulsion in the papermaking slurry is required to have a certain boiling point range, and more specifically, preferably has a boiling point of 50° C. to 200° C. at atmospheric pressure. If the boiling point is more preferably 60° C. to 190° C., the papermaking slurry is easily manipulated as an industrial production process, and can be removed comparatively efficiently by heating. If the boiling point of the oily compound at atmospheric pressure is lower than 50° C., it becomes necessary handle the papermaking slurry while controlling to a low temperature in order to ensure stable handling thereof, which is not desirable in terms of efficiency. Moreover, if the boiling point of the oily compound at atmospheric pressure exceeds 200° C., a considerable amount of energy is required to remove the oily compound by heating in the drying step, thereby also making this undesirable.

Moreover, a solubility of the aforementioned oily compound in water at 25° C. of preferably 2% by weight or less and more preferably 1% by weight or less is preferable from the viewpoint of contributing to efficient formation of a structure required by the oily compound.

Examples of oily compounds include hydrocarbons, linear saturated hydrocarbons, cyclic hydrocarbons, branched or cyclic unsaturated hydrocarbons and aromatic hydrocarbons having a number of carbon atoms within the range of 6 to 14, and monovalent, primary alcohols having a number of carbon atoms within the range of 5 to 9. In particular, the use of at least compound selected from among 1-pentanol, 1-hexanol and 1-heptanol enables the fine cellulose fiber porous sheet of the present invention to be produced particularly preferably. This is thought to be because these compounds are suitable for producing a non-woven fabric having high porosity and a fine porous structure since the oil droplet size of the emulsion is extremely small (1 μm or less under ordinary emulsification conditions).

These oily compounds may be incorporated as individual compounds or may be incorporated as a mixture of a plurality thereof. Moreover, a water-soluble compound may be dissolved in the papermaking slurry in order to control emulsion properties to a suitable state.

More specifically, one or more types of water-soluble compounds selected from the group consisting of sugars, water-soluble polysaccharides, water-soluble polysaccharide derivatives, polyvalent alcohols, alcohol derivatives and water-soluble polymers may be contained as water-soluble compounds. Here, water-soluble polysaccharides refer to polysaccharides that are soluble in water, and numerous types of compounds exist in the form of natural products as well. Examples thereof include starch, soluble starch and amylose. In addition, water-soluble polysaccharide derivatives include derivatives of the aforementioned water-soluble polysaccharides, such as alkylation products, hydroxyalkylation products and acetylation products that are soluble in water. Alternatively, polysaccharides that are insoluble in water prior to derivatization in the manner of cellulose or starch are also included in the water-soluble polysaccharide derivatives after having been made to be soluble in water by derivatization such as hydroxyalkylation, alkylation or carboxyalkylation. Water-soluble polysaccharide derivatives derived with two or more types of functional groups are also included. However, water-soluble compounds that can be used are not limited to the compounds described above.

The mixed amount of the aforementioned water-soluble compound is preferably 25% by weight or less relative to the oily compound. If added in an amount greater than this, the ability of the oily compound to form an emulsion decreases, thereby making this undesirable. In addition, the water-soluble compound is preferably dissolved in the aqueous phase in the papermaking slurry. The concentration of the water-soluble compound is preferably 0.003% by weight to 0.3% by weight, more preferably 0.005% by weight to 0.08% by weight and more preferably 0.006% by weight to 0.07% by weight, and if within these ranges, simultaneous to it being easier to obtain a fine cellulose fiber porous sheet, the state of the papermaking slurry is frequently stabilized, thereby making this preferable.

A surfactant other than the aforementioned water-soluble compound may be contained in the papermaking slurry for the purpose of stabilizing the emulsion such that the total amount in combination with the aforementioned specific water-soluble polymer is within the aforementioned concentration range.

Examples of surfactants include, but are not limited to, anionic surfactants such as alkyl sulfuric acid ester salts, polyoxyethylene alkyl sulfuric acid ester salts, alkylbenzene sulfonates or α-olefin sulfonates, cationic surfactants such as alkyltrimethylammonium chloride, dialkyldimethylammonium chloride or benzalkonium chloride, amphoteric surfactants such as alkyldimethylaminoacetate betaines or alkylamidodimethylaminoacetate betaines, and nonionic surfactants such as alkyl polyoxyethylene ethers or fatty acid glycerol esters.

Continuing, a description is provided of the step for adding the aforementioned water-dispersible blocked polyisocyanate to the papermaking or coating slurry. The concentration at which the previously described water-dispersible blocked polyisocyanate is added to the papermaking slurry can be arbitrarily changed within the range of 0.0001% by weight to 0.5% by weight provided there is no impairment of structure or performance of the fine cellulose fiber sheet of the present embodiment. Furthermore, the amount of the water-dispersible blocked polyisocyanate added is determined so that a prescribed weight of blocked polyisocyanate is contained in the sheet after the heat treatment step.

In addition, various additives may also be added to the papermaking slurry according to the specific objective. For example, a functionalization agent composed of the aforementioned water-repellent, oil-repellent processing agent, water-soluble polymer, antimicrobial polymer, thermoplastic resin, thermosetting resin or photocurable resin, an inorganic particulate compound in the manner of silica particles, alumina particles, titanium oxide particles or calcium carbonate particles, resin fine particles, various types of salts, organic solvents to a degree that does not inhibit the stability of the papermaking slurry or antifoaming agents can be added within a range that does not have a detrimental effect on the structure of the sheet structure (with respect to selection of type and selection of composition).

The composition of water in the papermaking slurry is 85% by weight to 99.9% by weight, preferably 90% by weight to 99.4% by weight, and more preferably 92% by weight to 99.2% by weight. If the composition of water in the papermaking slurry is lower than 85% by weight, there are many cases in which viscosity increases, making it difficult to uniformly disperse the fine cellulose fibers in the papermaking slurry, and making it difficult to obtain a fine cellulose fiber sheet having air permeability of a uniform structure, thereby making this undesirable. In addition, if the composition of water in the papermaking slurry exceeds 99.5% by weight, filtration time becomes extremely long and simultaneous to a considerable decrease in productivity, film quality uniformity also becomes quite poor, thereby making this undesirable.

In addition, in the case of a coating slurry, the composition of water is preferably 70% by weight to 99.8% by weight and more preferably 75% by weight to 99.6% by weight.

Examples of methods used to prepare the papermaking or coating slurry include (1) a method consisting of mixing a preliminarily prepared aqueous solution containing additives with a fine cellulose fiber aqueous dispersion and dispersing to obtain a papermaking slurry, and (2) a method consisting of individually adding various types of additives one at a time while stirring a fine cellulose fiber aqueous dispersion. Furthermore, in the case of adding a plurality of types of additives, there is the potential for the dispersed state and zeta potential of the papermaking slurry to change depending on the order in which the additives are added in a system that allows additives to aggregate (such as a system in which a cationic polymer and an anionic polymer form an ion complex). However, there are no particular limitations on the order and amounts in which they are added, and are preferably added using a method that allows the obtaining of the desired dispersed state and sheet properties of the papermaking slurry.

Examples of stirring devices for uniformly mixing and dispersing the aforementioned additives include dispersers and high-pressure homogenizers of a type that causes blades having a cutting function to rotate at high speed in the manner of an agitator, homomixer, pipeline mixer or blender. When stirring, the average dispersed diameter of the slurry is preferably 1 μm to 300 μm. However, since excessive stirring can cause excessive shear force to be applied to an emulsion of the water-dispersible blocked polyisocyanate and the like and result in the risk of a breakdown of the emulsion structure thereof, it is preferable to not use a high-pressure homogenizer, grinder-type diameter reduction device or millstone-type grinding device and the like.

Next, an explanation is provided of the papermaking step for forming wet paper by filtration on a porous base material of the papermaking slurry.

This papermaking step may basically be carried out using any type of device provided the procedure consists of removing the water from a papermaking slurry, and using a filter or filter cloth (also referred to as a wire in the technical field of papermaking) so as to retain fine cellulose fibers.

The use of a device such as an inclined wire-type papermaking machine, Fourdrinier papermaking machine or cylinder papermaking machine for the papermaking machine preferably allows the obtaining of a fine cellulose fiber sheet in the form of a sheet having few defects. The papermaking machine may be of the continuous type or batch type, and may be used according to the specific objective.

Although dehydration is carried out by the papermaking step using the fine cellulose fiber papermaking slurry obtained in the aforementioned preparation step, since the papermaking step is a step for filtering dry aggregates of fine cellulose fibers and the like dispersed in the papermaking slurry using a wire or filter cloth, the size of the openings in the wire or filter cloth is important. In the present invention, any wire or filter cloth can essentially be used provided papermaking can be carried out in which the yield percentage of insoluble components, including fine cellulose fibers contained in the papermaking slurry, is 70% by weight or more, preferably 95% by weight or more and more preferably 99% by weight or more.

However, even if the yield percentage of the fine cellulose fibers and the like is 70% by weight or more, since papermaking takes a considerable amount of time and production efficiency becomes considerably poor unless filterability is high, if water permeability of the wire or filter cloth at atmospheric pressure and 25° C. is preferably 0.005 ml/(cm$^2$·sec) or more and more preferably 0.01 ml/(cm$^2$·sec) or more, papermaking can be made to be preferable from the viewpoint of productivity. If the yield percentage of the aforementioned insoluble components is lower than 70% by weight, not only productivity become quite poor, insoluble components such as fine cellulose fibers ends up clogging the wire or filter cloth used, thereby significantly exacerbating separability of the fine cellulose fiber sheet following production.

Here, water permeability of the wire or filter cloth at atmospheric pressure is evaluated in the manner indicated below. When installing the wire or filter cloth to be evaluated in a batch-type papermaking machine (such as the Automated Square Sheet Machine manufactured by Kumagai Riki Kogyo Co., Ltd.), the wire is placed as is in the case of a wire, while in the case of a filter cloth, the filter cloth is placed on a 80 to 120 mesh metal mesh (having hardly any filtration resistance), an adequate amount of water (defined as y (ml)) is injected into the papermaking machine having a papermaking area of x (cm$^2$), and drainage time is measured at atmospheric pressure. Water permeability in the case of a drainage time of z (sec) is defined as $y/(x \cdot z)$ (ml/(cm$^2$·s).

Examples of wires or filter cloths that can be used for extremely fine cellulose fibers include, but are not limited to, the Tetex Mono DLW07-8435-SK010 (made of PET) manufactured by Sefar AG (Switzerland) and NT20 (PET/nylon blend) manufactured by Shikishima Canvas Co., Ltd.

Although the fine cellulose fiber sheet of the present embodiment can have the aforementioned organic polymer sheet layer arranged therein, papermaking is more preferably carried out by using an organic polymer fiber sheet layer made of cellulose, nylon or polyester and the like as a support in particular. In this case, it is sufficient to select a material for the wire or filter cloth of the papermaking machine that is capable of satisfying requirements relating to yield percentage and water permeability in combination with the support.

In the dehydration of the papermaking step, solidification progresses and a concentrated composition in the form of wet paper is obtained in which the solid content has been increased beyond that of the fine cellulose fiber concentration and papermaking slurry. The solid content of the wet paper controls the degree of dehydration according to the papermaking suction pressure (wet suction or traction) and pressing step, and the solid content concentration is adjusted to preferably be within the range of 6% by weight to 25% by weight and more preferably 8% by weight to 20% by weight. If the solid content of the wet paper is lower than 6% by weight, the wet paper is no longer self-standing resulting in increased susceptibility to the occurrence of problems during processing. In addition, if dehydration proceeds to a concentration at which the solid content of the wet paper exceeds 25% by weight, uniformity ends up being lost as a result of the presence of an aqueous layer in the vicinity of the fine cellulose fibers instead of an aqueous phase only.

In addition, a method may also be used in which papermaking is carried out on filter cloth, and water in the resulting wet paper is replaced with an organic solvent in an organic solvent substitution step followed by drying. The details of this method are in accordance with International Publication No. WO 2006/004012 filed by the inventors of the present invention.

Furthermore, in the case of using the organic polymer fiber sheet layer as a support, the support is placed in a papermaking machine installed with a wire or filter cloth, a portion of the water that composes the papermaking slurry is dehydrated (made into paper) on the support, wet paper of a sheet composed of fine cellulose fibers is laminated on the support and integrated into a single unit to produce a multilayer sheet composed of at least two layers of a multilayer structure. A support having two or more layers of multilayer structures is used to produce a multilayer sheet having three or more layers. In addition, a multilayer layer sheet of three or more layers may be obtained by carrying out multiple stages of papermaking on two or more layers of the fine cellulose fiber sheet of the present invention on the support.

Continuing, an explanation is provided of the drying step. The wet paper obtained in the previously described papermaking step is transformed into a fine cellulose fiber sheet by evaporating a portion of the water in a drying step using heat. If a fixed length drying type of dryer of a type that is capable of drying water with the width being of a fixed length in the manner of a drum dryer or pin tenter is used in the drying step, a fine cellulose fiber sheet having high air permeability resistance can be stably obtained, thereby making this preferable. Although suitably selected according to the conditions, if the drying temperature is preferably made to be within the range of 45° C. to 180° C. and more preferably 60° C. to 150° C., a fine cellulose fiber sheet having preferable air permeability can be produced. If the drying temperature is lower than 45° C., adequate productivity cannot be secured since the water evaporation rate is excessively slow in many cases, thereby making this undesirable, while if the drying temperature is higher than 180° C., the hydrophilic polymer composing the structure may end up undergoing thermal degradation, and since energy efficiency, which has an effect on cost, also decreases, this is also not preferable. Carrying out composition preparation by low-temperature drying at 100° C. or lower and carrying out multistage drying at a temperature of 100° C. or higher in the next stage is also effective in terms of obtaining a highly uniform fine cellulose fiber sheet.

Chemical bonds are formed between the blocked polyisocyanate and fine cellulose fibers contained in the sheet by subjecting the sheet obtained in the aforementioned drying step to heat treatment. In addition, immobilization of a functionalization agent inside and/or on the surface of the sheet and crosslinking between the organic polymer sheet and the fine cellulose fiber sheet in the laminated structure also proceed simultaneous thereto due to the blocked polyisocyanate.

The heat treatment step preferably uses a fixed length drying type of heat treatment device of a type that is capable of heating with the width being of a fixed length in the manner of a drum dryer or pin tenter from the viewpoints of uniform heat treatment and inhibiting shrinkage of the sheet caused by heating. Furthermore, in the case of using a dryer in the manner of a drum dryer, heat treatment can be adjusted by adjusting feeding speed and roller diameter.

As has been previously described, although the blocked polyisocyanate is stable at normal temperatures, it is able to form chemical bonds with functional groups having an active hydrogen as a result of dissociation of blocking groups and regeneration of isocyanate groups when subjected to heat treatment at a temperature equal to or higher than the dissociation temperature of the blocking agent. Although varying according to the blocking agent used, the heating temperature is preferably within the range of 80° C. to 220° C. and more preferably 100° C. to 180° C., and the blocked polyisocyanate is heated to a temperature equal to or higher than the dissociation temperature of the blocking groups. In the case of heating at a temperature lower than the dissociation temperature of the blocking groups, crosslinking does not occur since isocyanate groups are not regenerated. On the other hand, if heated to a temperature higher than 220° C., the fine cellulose fibers and blocked polyisocyanate undergo thermal deterioration and may become colored, thereby making this undesirable.

The heating time is preferably 15 seconds to 10 minutes and more preferably 30 seconds to 2 minutes. Heating time can be shortened in the case the heating temperature is sufficiently higher than the dissociation temperature of the blocking groups. In addition, in the case the heating temperature is 130° C. or higher, since heating for 2 minutes or longer results in a dramatic reduction in moisture in the sheet, the sheet becomes brittle immediately after heating which may result in handling difficulties, thereby making this undesirable.

In addition, a smoothing step may also be provided for carrying out smoothing treatment with a calendering device on the fine cellulose fiber sheet obtained in the aforementioned drying step. As a result of going through the smoothing step, the surface is smoothened allowing the obtaining of a fine cellulose fiber sheet having reduced thickness. Namely, by further including a step for carrying out smoothing treatment using a calendering device on the fine cellulose fiber sheet after drying, thickness can be reduced, thereby making it possible to provide the fine cellulose fiber sheet of the present invention over a wide range of combinations of thickness, air permeability and strength. For example, a fine cellulose fiber sheet can be easily produced that has a thickness of 20 μm or less (and a lower limit thickness of about 3 μm) at basis weight setting of 10 g/m² or less. In addition to an ordinary calendering device using a single press roller, a super calendering device may also be used that has a structure in which these are installed in multiple stages. A fine cellulose fiber sheet can be obtained that maintains a balance among numerous types of properties by selecting these devices, the respective materials on both sides of the rollers during calendering treatment (such as material hardness) and line pressure according to the specific objective. In addition, the aforementioned heat treatment step may be carried out simultaneous to calendering treatment.

As a result of satisfying the aforementioned conditions, a fine cellulose fiber sheet can be provided that contains aggregates of blocked polyisocyanates therein, and in which crosslinked structures are formed by chemical bonding between all or a portion of the blocked polyisocyanate and the fine cellulose fibers by carrying out heat treatment on the fine cellulose fiber sheet.

EXAMPLES

The following provides a detailed explanation of the present invention by indicating examples thereof.

Furthermore, important measured values of physical properties were measured using the methods indicated below.

(1) Number Average Fiber Diameter of Fine Cellulose Fibers

The surface of a multilayered structure composed of fine cellulose fibers was observed with a scanning electron microscope (SEM) at three random locations at a magnification factor of 1,000 to 100,000 corresponding to the fiber diameter of the fine fibers. Lines were drawn in the horizontal and vertical directions relative to the screen on the resulting SEM image, the fiber diameter of fibers intersecting the lines was measured from an enlarged image, and the number of intersecting fibers and the fiber diameter of each fiber were counted. Number average fiber diameter was then calculated using two series of vertical and horizontal measurement results for a single image. Number average fiber diameter was calculated in the same manner for two other extracted SEM images, and the results for the total of three images were averaged and used as the average fiber diameter of the target sample.

(2) Basis Weight

Sheet basis weight was evaluated by calculating in compliance with JIS P 8124.

(3) Papermaking Ability

Papermaking ability was evaluated by measuring drainage time during papermaking. A papermaking slurry prepared based on a cellulose sheet having a basis weight of 10 g/m² was loaded into a batch-type papermaking machine (Automated Square Sheet Machine, 25 cm×25 cm, 80 mesh, Kumagai Riki Kogyo Co., Ltd.) installed with a PET/nylon blend plain weave fabric (NT20, water permeability at 25° C. under atmospheric pressure: 0.03 ml/cm²·s, capable of filtering off 99% or more of fine cellulose fibers by filtering at 25° C. under atmospheric pressure, Shikishima Canvas Co., Ltd.) followed by carrying out papermaking (dehydration) using a degree of vacuum of 4 KPa relative to atmospheric pressure. The amount of time required for drainage at this time was measured as drainage time.

Drainage time of a system to which was added water-dispersible blocked polyisocyanate relative to drainage time in the case of not adding water-dispersible blocked polyisocyanate was evaluated as A when it was less than 50%, evaluated as B when it was less than 80%, and evaluated as C when it was 80% or more.

(4) Tensile Strength Wet/Dry Ratio

First, evaluation of dry tensile strength was carried out by measuring 10 sample locations over a width of 15 mm using the Desktop Horizontal Tensile Tester (No. 2000) manufactured by Kumagai Riki Kogyo Co., Ltd. in accordance with the method defined in JI P 8113, and the average value thereof was taken to be the value of dry strength (N/15 mm). In addition, 10 sample locations on a sheet immersed for 5 minutes in a container filled with an adequate amount of water for submerging the sheet were measured using the same method, and the average value thereof was taken to be the value of wet strength (N/15 mm).

Wet/dry strength ratio was then calculated from the evaluated dry strength and wet strength according to the equation indicated below.

$$\text{Wet/dry strength ratio (\%)} = (\text{wet strength})/(\text{dry strength}) \times 100$$

Here, the dry strength and wet strength are not converted to values corresponding to a basis weight of 10 g/m².

Dry strength was evaluated as A when it was 70% or more, evaluated as B when it was 50% or more, and evaluated as C when it was less than 50%.

(5) Wet/Dry Strength Ratio after Solvent Immersion

A sample measuring 25 cm×25 cm was immersed in a container filled with dimethylformamide for one day.

Subsequently, the sample was allowed to dry in a vacuum at room temperature followed by calculation of tensile strength wet/dry ratio using the procedure described above. Wet/dry strength ratio was evaluated as A when it was 70% or more, evaluated as B when it was 50% or more and evaluated as C when it was less than 50%.

(6) Evaluation of Distribution of Blocked Polyisocyanate in Sheet

First, four locations were randomly selected on a sheet measuring 25 cm×25 cm followed by collecting samples measuring 1 cm on a side. Three-dimensional TOF-SIMS analysis was then carried out on the four samples.

[Planar Direction Uniformity]

The number of counts (C1) at m/z=26 (fragment ion: CN) derived from blocked polyisocyanate and the number of counts (C2) at m/z=59 (fragment ion: $C_2H_3O_2$) derived from cellulose were standardized for C2 in the four samples. Planar direction uniformity was evaluated as A when the coefficient of variation of the value of C1/C2 of each sample was less than 50% and evaluated as C when it was 50% or more.

[Thickness Direction Uniformity]

C1/C2 was calculated for an upper portion, middle 1.0 portion and lower portion obtained when dividing the sheet into three equal portions in the direction of thickness for the four samples. C1 and C2 represented the number of counts (C1) at m/z=26 (fragment ion: CN) derived from blocked polyisocyanate and the number of counts (C2) at m/z=59 (fragment ion: $C_2H_3O_2$) derived from cellulose. Moreover, the average of C1/C2 was respectively calculated for the upper, middle and lower portions of the four samples. At this time, thickness direction uniformity was evaluated as A when the coefficient of variation for the three average values was less than 50% and evaluated as C when it was 50% or more.

The measurement conditions used for TOF-SIMS were as indicated below.

(Measurement Conditions)
- Instrument used: NanoTOF (Ullvac-Phi Inc.)
- Primary ion: $Bi_3^{++}$
- Accelerating voltage: 30 kV
- Ion current: Approx. 0.1 nA (DC)
- Analyzed area: 200 μm×200 μm
- Analysis time: Approx. 6 sec/cycle
- Detected ions: Anions
- Neutralization: Use of electron gun (Sputtering Conditions)
- Sputter ion: $Ar2500^+$
- Accelerating voltage: 20 kV
- Ion current: Approx. 5 nA
- Sputtered area: 600 μm×600 μm
- Sputtering time: 60 sec/cycle
- Neutralization: Use of electron gun (7) Laminate Adhesion A piece of a fine cellulose fiber sheet laminated onto an organic polymer sheet was cut out to a size of 5 cm×5 cm, immersed in a plastic bottle containing 100 ml of distilled water, and shaken for 1 day at a shaking speed of 200 rpm. Following shaking, the presence or absence of separation of the fine cellulose fiber sheet and organic polymer sheet was observed visually. The absence of separation was evaluated as A while the presence of separation was evaluated as C.

The experimental conditions and experimental results for Examples 1 to 11 and Comparative Examples 1 to 5 are shown in the following Table 1.

Example 1

Linter pulp was immersed in water to a concentration of 10% by weight, subjected to heat treatment for 4 hours at 130° C. in an autoclave and the resulting resin pulp was rinsed several times with water to obtain a wet pulp immersed in water.

The resin pulp was dispersed in water (40 L) to a solid content of 1.5% by weight, and the 400 L of dispersion were subjected to beating treatment for 20 minutes using the Model SDR14 Lab Refiner (pressurized disk type) manufactured by Aikawa Iron Works Co., Ltd. for the disc refiner device at a clearance between disks of 1 nmm. Continuing therefrom, beating treatment was continued under conditions of reducing the disk clearance to nearly zero. Samples were collected over time, and when CSF values were evaluated for the slurry samples according to the Canadian standard pulp freeness test method defined in JIS P 8121 (to be referred to as the CSF method), CSF values were confirmed to demonstrate a tendency by which they decreased over time, approached zero and then increased when beating was continued. Beating treatment was continued under the aforementioned conditions for 10 minutes after the clearance approached zero to obtain an aqueous beating dispersion having a CSF value of 73 ml↑. The resulting aqueous beating dispersion was subjected to five rounds of diameter reduction treatment at an operating pressure of 100 MPa using a high-pressure homogenizer (Model NS015H, Niro Soavi S.P.A. (Italy)) to obtain an aqueous dispersion of fine cellulose fibers (solid content concentration: 1.5% by weight).

Moreover, after diluting the aforementioned aqueous dispersion to a solid content concentration of 0.2% by weight, 312.5 g of the diluted dispersion were stirred with a Three-One Motor stirrer followed by dropping in 1.9 g of cationic blocked polyisocyanate (trade name: "Meikanate WEB", Meisei Chemical Works, Ltd., diluted to solid content concentration of 1.0% by weight) and stirring for 3 minutes to obtain a papermaking slurry (total of 314.4 g). The weight ratio of the added cationic blocked polyisocyanate was 3% by weight based on the weight of the cellulose solid fraction.

The papermaking slurry prepared in the manner described above was loaded into a batch-type papermaking machine (automated angle-type sheet machine, 25 cm×25 cm, 80 mesh, Kumagai Riki Kogyo Co., Ltd.) installed with a blended PET/nylon plain weave fabric (NT20, water permeability at 25° C. under atmospheric pressure: 0.03 ml/cm²·s, capable of filtering off 99% or more of fine cellulose fibers by filtering at 25° C. under atmospheric pressure, Shikishima Canvas Co., Ltd.) based on a cellulose sheet having a basis weight of 10 g/m² followed by carrying out papermaking (dehydration) at a degree of vacuum of 4 KPa relative to atmospheric pressure.

The resulting wet paper composed of a concentrated composition in a wet state present on the filter cloth was separated from the wire and pressed for 1 minute at a pressure of 1 kg/cm² followed by positioning the wet paper surface so as to contact the drum surface, drying for about 120 seconds in the state of two layers consisting of the wet paper and filter cloth with the wet paper again in contact with the drum surface of a drum dryer set to a surface temperature of 130° C., and separating the filter cloth from the resulting dried cellulose sheet-like structure composed of two layers to obtain a fine cellulose fiber sheet (25 cm×25 cm) composed of uniformly white fine cellulose fibers. When the surface of this dry sheet was analyzed by an SEM image obtained at a magnification factor of 10,000×, the number average fiber diameter of fine cellulose fibers on the surface of the fine cellulose fibers was 110 nm.

Moreover, the aforementioned dry sheet was subjected to heat treatment for 2 minutes at 160° C. in an oven after sandwiching between two SUS steel frames (25 cm×25 cm) and immobilizing with a clip to obtain a fine cellulose fiber sheet S1 crosslinked with blocked polyisocyanate. The papermaking ability, wet/dry strength ratio, wet/dry strength ratio after solvent immersion and blocked polyisocyanate distribution thereof were all superior.

Example 2

Diameter reduction, papermaking slurry preparation, papermaking, drying and heat treatment were carried out in the same manner as Example 1 with the exception of making the added amount of cationic blocked polyisocyanate to be 6.3 g (10% by weight based on the weight of the cellulose solid fraction to obtain S2. Papermaking ability, wet/dry strength ratio, wet/dry strength ratio after solvent immersion and block polyisocyanate distribution were all superior. In addition, a graph indicating the relationship of variations in C1/C2 in the direction of depth for one of the four sample sites of S2 analyzed by TOF-SIMS is shown in FIG. 1. Although the C1/C2 ratio was indicated to be large only on the uppermost surface of the upper portion of the sheet, it subsequently became stable and demonstrated a value of C1/C2 ≑ 0.2. On the basis thereof, it can be said that, although blocked polyisocyanate is present in comparatively large amounts on the uppermost surface of the sheet, it is distributed uniformly over a broad range within the sheet. C1/C2 gradually increased moving towards the back of the sheet. Ideally, C1/C2 ought to increase only on the uppermost surface in the same manner as in the upper portion of the sheet. However, this is thought to be the result of fragment ions, formed starting from the outermost surface where there is a large amount of blocked polyisocyanate, being observed quickly due to the presence of minute gaps between the fibers. In actuality, as a result of having analyzed the back of the sheet in the same manner by TOF-SIMS, a similar graph was obtained. Thus, it can be concluded that blocked polyisocyanate present in slightly larger amounts on the uppermost surfaces of the sheet and is distributed uniformly over a broad range inside the sheet.

Example 3

Diameter reduction, papermaking slurry preparation, papermaking, drying and heat treatment were carried out in the same manner as Example 1 with the exception of making the added amount of cationic blocked polyisocyanate to be 19 g (30% by weight based on the weight of the cellulose solid fraction) to obtain S3. Papermaking ability, wet/dry strength ratio, wet/dry strength ratio after solvent immersion and blocked polyisocyanate distribution were all superior.

Example 4

Diameter reduction, papermaking slurry preparation, papermaking, drying and heat treatment were carried out in the same manner as Example 1 with the exception of selecting a different cationic blocked polyisocyanate (trade name: "Meikanate CX", Meisei Chemical Works, Ltd., diluted to solid content concentration of 1.0% by weight) and making the added amount thereof to be 6.3 g (10% by weight based on weight of cellulose solid fraction) to obtain S4. Despite changing the type of blocked polyisocyanate, papermaking ability, wet/dry strength ratio, wet/dry strength ratio after solvent immersion and blocked polyisocyanate distribution were all superior.

Example 5

Fiber reduction, papermaking slurry preparation, papermaking, drying and heat treatment were carried out in the same manner as Example 1 with the exception of using tencel cut yarn (length: 3 mm) for the raw material pulp to obtain S5. Despite using fine cellulose fibers having a larger fiber diameter, papermaking ability, wet/dry strength ratio, wet/dry strength ratio after solvent immersion and blocked polyisocyanate distribution were all superior.

Example 6

Fiber reduction, papermaking slurry preparation, papermaking, drying and heat treatment were carried out in the same manner as Example 1 with the exception of using manila hemp pulp for the raw material pulp to obtain S6. Despite using fine cellulose fibers having a smaller fiber diameter, papermaking ability, wet/dry strength ratio, wet/dry strength ratio after solvent immersion and blocked polyisocyanate distribution were all superior.

Example 7

A dispersion of fine cellulose fibers produced from linter pulp (solid content concentration: 0.2% by weight) and a dispersion of fine cellulose fibers produced from tencel cut yarn (solid content concentration: 0.2% by weight) were respectively obtained using the fine cellulose fiber production method described in Example 1. Continuing, each of the aqueous dispersions was mixed to produce a mixed slurry. The mixing ratio was adjusted so that fine cellulose fibers derived from linter pulp accounted for 60% by weight and the fine cellulose fibers derived from tencel cut yarn accounted for 40% by weight. The resulting mixed slurry was vigorously mixed for 4 minutes with a home blender. 312.5 g of this mixed slurry (solid content concentration: 0.2% by weight, 0.14% by weight derived from linter pulp. 0.06% by weight derived from tencel cut yarn) were stirred with a Three-One Motor stirrer and 1.9 g of cationic blocked polyisocyanate (Meikanate WEB, diluted to solid content concentration of 1.0% by weight) equivalent to 3% by weight based on the weight of the cellulose solid fraction were dropped in followed by stirring for 3 minutes to obtain a papermaking slurry (total weight: 314.4 g). Subsequently, papermaking, drying and heat treatment were carried out in the same manner as Example 1 to obtain S7. Despite using two types of fine cellulose fibers having different fiber diameters, papermaking ability, wet/dry strength ratio, wet/dry strength ratio after solvent immersion and blocked polyisocyanate distribution were all superior.

Example 8

Papermaking was carried out by laminating a fine cellulose fiber sheet on a base material in the form of cupra long fiber (filament) non-woven fabric (trade name: Bemliese SA14G, Asahi Kasei Fibers Corp., basis weight: 14 g/m$^2$, film thickness: 70 μm, density: 0.2 g/cm$^3$, average single fiber fineness: 0.2 dtex). After diluting the aqueous dispersion of fine cellulose fibers in Example 1 (solid content concentration: 1.5% by weight) to a solid content concentration of 0.1% by weight based on the formation of a fine cellulose fiber sheet having a basis weight of 5 g/m$^2$, 312.5 g of the diluted aqueous dispersion were stirred with a Three-One Motor stirrer and 0.95 g of cationic blocked polyisocyanate (trade name: "Meikanate WEB", Meisei Chemical Works, Ltd., diluted to solid content concentration of 1.0% by weight) were dropped in followed by stirring for 3 minutes to obtain a papermaking slurry (total weight: 313.5 g). A filter cloth in the form of a blended PET/nylon plain weave fabric (NT20, water permeability at 25° C. under atmospheric pressure: 0.03 ml/cm$^2$·s, Shikishima Canvas Co., Ltd.) was installed in a batch-type papermaking machine (automated angle-type sheet machine, 25 cm×25 cm, 80 mesh, Kumagai Riki Kogyo Co., Ltd., papermaking area: 25 cm×25 cm, 80 mesh), and the previously described nylon sheet was spread thereon followed by loading with the aforementioned papermaking slurry. Papermaking (dehydration) was then carried out at a degree of vacuum of 4 KPa relative to atmospheric pressure. The same filter cloth was placed over the resulting wet paper having a bilayer structure formed on the filter cloth, and after pressing the wet paper from both sides while sandwiched between the filter cloth for 1 minute at a pressure of 1 kg/cm$^2$, the wet paper was dried for about 120 seconds with a drum dryer set to a surface temperature of 130° C. so as to contact the drum surface while in the state of three layers consisting of filter cloth, wet paper and filter cloth in that order. The filter cloths on both sides were able to be easily separated from the resulting three-layer sheet to obtain a dried sample. Moreover, heat treatment was carried out on this sample in the same manner as Example 1 to obtain S8. Papermaking ability and blocked polyisocyanate distribution were superior. Moreover, the cupra long fiber nonwoven fabric and fine cellulose fiber sheet did not separate even after immersing in water. Furthermore, since wet/dry strength ratio and wet/dry strength ratio after solvent immersion were unable to be calculated for the fine cellulose fibers alone as a result of being a laminate, these two parameters were not evaluated.

Example 9

1-hexanol and hydroxypropylmethyl cellulose (trade name: "60SH-4000", Shin-Etsu Chemical Co., Ltd.) were added to the diluted aqueous dispersion (312.5 g) of Example 1 at 1.2% by weight (3.9 g) and 0.012% by weight (0.039 g), respectively, followed by emulsifying and dispersing for 4 minutes with a home blender. Subsequently, 1.9 g of cationic blocked polyisocyanate (Meikanate WEB, diluted to solid content concentration of 1.0% by weight), equivalent to 3% by weight based on the weight of the cellulose solid fraction, were added and stirred. The remainder of the procedure consisted of carrying out papermaking, drying and heat treatment using this papermaking slurry in the same manner as Example 1 to obtain S9. Despite using emulsion papermaking, papermaking ability, wet/dry strength ratio, wet/dry strength ratio after solvent immersion and blocked polyisocyanate distribution were all superior.

Example 10

Diameter reduction, papermaking slurry preparation, papermaking, drying and heat treatment were carried out in the same manner as Example 1 with the exception of selecting a nonionic blocked polyisocyanate (trade name: "MF-25K", DKS Co., Ltd., diluted to solid content concentration of 1.0% by weight) and making the added amount thereof to be 1.9 g (3% by weight based on weight of cellulose solid fraction) to obtain S10. As a result of changing the type of blocked polyisocyanate, although papermaking ability, wet/dry strength ratio and wet/dry strength ratio after solvent immersion were inferior to that of cationic blocked polyisocyanate, they were within the allowable ranges. On the other hand, blocked polyisocyanate distribution was uniform.

Example 11

In the production of the papermaking slurry of Example 1, 1.9 g of anionic blocked polyisocyanate (trade name: "E-37", DKS Co., Ltd., diluted to a solid content concentration of 1.0% by weight), equivalent to 3% by weight relative to the weight of the cellulose solid fraction, were added and stirred for 3 minutes followed by adding 0.19 g of a cationic polymer in the form of a polydiallyl-dimethyl ammonium chloride polymer (trade name: "PAS-H-10L", Nittobo Medical Co., Ltd., diluted solution having a solid content concentration of 1.0% by weight), equivalent to 0.3% by weight based on the weight of the cellulose solid fraction, and stirring for 3 minutes. The remainder of the procedure consisted of carrying out the same method as Example 1 using this papermaking slurry to obtain S11. Although an anionic blocked polyisocyanate was used, the use of a cationic polymer made it possible to demonstrate papermaking ability, wet/dry strength ratio, wet/dry strength ratio after solvent immersion and blocked polyisocyanate distribution were superior in the same manner as in the case of using a cationic blocked polyisocyanate.

Comparative Example 1

Papermaking, drying and heat treatment were carried out in the same manner as Example 1 with the exception of not adding cationic blocked polyisocyanate to obtain R1. Papermaking ability, wet/dry strength ratio and wet/dry strength ratio after solvent immersion were inferior. This was due to being unable to undergo chemical crosslinking as a result of not containing a blocked polyisocyanate.

Comparative Example 2

Diameter reduction, papermaking slurry preparation, papermaking, drying and heat treatment were carried out in the same manner as Example 1 with the exception of adding 1.9 g of a cationic polyurethane emulsion (trade name: "Superflex 650", DKS Co., Ltd., diluted to a solid content concentration of 1.0% by weight) instead of cationic blocked polyisocyanate to obtain R2. Although wet/dry strength ratio was superior, due to the absence of chemical bonding with fine cellulose fibers, solvent resistance was low and the polyurethane emulsion eluted, thereby resulting in poor wet/dry strength ratio after solvent immersion.

Comparative Example 3

Diameter reduction, papermaking slurry preparation, papermaking, drying and heat treatment were carried out in the same manner as Example 8 with the exception of not adding cationic blocked polyisocyanate to obtain R3. Since crosslinks were not formed by blocked polyisocyanate, the cupra long fiber non-woven fabric and fine cellulose fiber sheet separated. In addition, since a blocked polyisocyanate was not added, there was no change in papermaking ability. Furthermore, since wet/dry strength ratio and wet/dry strength ratio after solvent immersion were unable to be calculated for the fine cellulose fibers alone as a result of being a laminate, these two parameters were not evaluated.

Comparative Example 4

The papermaking slurry of Example 2 was subjected to papermaking and drying without adding cationic blocked polyisocyanate to obtain 0.63 g of a sheet measuring 25 cm×25 cm composed of fine cellulose fibers. This sheet was immersed for 3 minutes in a dipping bath containing an aqueous dispersion of cationic blocked polyisocyanate (trade name: "Meikanate WEB", diluted to a solid content concentration of 2.1% by weight) and after lifting the sheet out of the bath, excess treatment liquid was absorbed with filter paper. After sandwiching between metal frames made of SUS measuring 25 cm on a side, the sheet was dried at 40° C. Heat treatment was then carried out for 2 minutes at 160° C. to obtain R4. Furthermore, the amount of absorbed liquid after absorbing the excess liquid with filter paper was 3.5 g, the amount of cationic blocked polyisocyanate adhered to the sheet calculated on the basis thereof was 0.06 g. Namely, the sheet contained 10% by weight of cationic blocked polyisocyanate based on the weight of the cellulose solid fraction. As a result of analyzing by TOF-SIMS, there was little variation in C1/C2 in the planar direction in the case of the post-processing method. On the other hand, although there was an extremely large amount of blocked polyisocyanate in the upper and lower portions of the sheet in the direction of thickness, the amount was quite low in the middle portion of the sheet, and there was considerable variation among the upper, middle and lower portions. The presence of a portion containing a low amount of blocked polyisocyanate resulted in a decrease in wet/dry strength ratio. A graph indicating the relationship of variations in C1/C2 in the direction of depth for one of the four sample sites of R4 analyzed by TOF-SIMS is shown in FIG. 1. The results were such that C1>>C2 (C1/C2>10), indicating that the sheet surface was completely covered by blocked polyisocyanate. There was hardly any blocked polyisocyanate present when measurement reached the middle portion and C1/C2 ≒ 0.04. C1/C2 gradually increased moving towards the back of the sheet in the same manner as Example 2. Furthermore, the reason for the increasing tendency being greater than that in Example 2 is thought to be the result of a larger number of fragment ions having been quickly observed since the amount of blocked polyisocyanate on the uppermost surfaces was much greater than in Example 2. A graph similar to that of FIG. 1 was obtained as a result of having analyzed the back of the sheet in the same manner by TOF-SIMS. Thus, although a large amount of blocked polyisocyanate is present on the uppermost surfaces when using the post-processing method, hardly any had permeated inside the sheet. Namely, in the case of the post-processing method, it is difficult to have blocked polyisocyanate uniformly distributed in the direction of thickness as in the internal addition method.

Comparative Example 5

Diameter reduction, papermaking slurry preparation, papermaking, drying and heat treatment were carried out in the same manner as Example 11 with the exception of not adding the cationic polymer in the form of polydiallyldimethyl ammonium chloride copolymer to obtain R5. Since the anionic blocked polyisocyanate did not adhere to the fine cellulose fibers, papermaking ability, wet/dry strength ratio and wet/dry strength ratio after solvent immersion were all inferior. In addition, distribution of blocked polyisocyanate was unable to be measured.

TABLE 1

| | Sample Name | Fine Cellulose Fiber Type | Concentration (wt %) | Blocked Polyisocyanate Aqueous Dispersion Type | Concentration (wt %) | Addition method | Other Additives Type | Concentration (wt %) | Addition method |
|---|---|---|---|---|---|---|---|---|---|
| Ex. 1 | S1 | Linter pulp | 0.2 | Meikanate WEB | 3.0 | Internal | — | — | — |
| Ex. 2 | S2 | Linter pulp | 0.2 | Meikanate WEB | 10.0 | Internal | — | — | — |
| Ex. 3 | S3 | Linter pulp | 0.2 | Meikanate WEB | 30.0 | Internal | — | — | — |
| Ex. 4 | S4 | Linter pulp | 0.2 | Meikanate WEB | 10.0 | Internal | — | — | — |
| Ex. 5 | S5 | Tencel | 0.2 | Meikanate WEB | 3.0 | Internal | — | — | — |
| Ex. 6 | S6 | Manilla hemp | 0.2 | Meikanate WEB | 3.0 | Internal | — | — | — |
| Ex. 7 | S7 | Linter pulp/tencel | 0.14/0.06 | Meikanate WEB | 3.0 | Internal | — | — | — |
| Ex. 8 | S8 | Linter pulp | 0.1 | Meikanate WEB | 3.0 | Internal | — | — | — |
| Ex. 9 | S9 | Linter pulp | 0.2 | Meikanate WEB | 3.0 | Internal | Oily compound*[1] | *1 | Internal |
| Ex. 10 | S10 | Linter pulp | 0.2 | MF-25K | 3.0 | Internal | — | — | — |
| Ex. 11 | S11 | Linter pulp | 0.2 | E-37 | 3.0 | Internal | Polycation*[3] | 0.3 | Internal |
| Comp. Ex. 1 | R1 | Linter pulp | 0.2 | — | — | — | — | — | — |
| Comp. Ex. 2 | R2 | Linter pulp | 0.2 | — | — | — | Superflex 650 | 3.0 | Internal |
| Comp. Ex. 3 | R3 | Linter pulp | 0.1 | — | — | — | — | — | — |
| Comp. Ex. 4 | R4 | Linter pulp | 0.2 | Meikanate WEB | 10*[2] | Immersion | — | — | — |
| Comp. Ex 5 | R5 | Linter pulp | 0.2 | E-37 | 3.0 | Internal | — | — | — |

| | Base Material | Avg. Fiber Diameter nm | Basis Weight g/m² | Papermaking Ability | Wet/Dry Strength Ratio | Wet/Dry Strength Ratio after Solvent Immersion | Blocked Polyisocyanate Distribution Planar | Blocked Polyisocyanate Distribution Thickness | Laminate Adhesion |
|---|---|---|---|---|---|---|---|---|---|
| Ex. 1 | — | 110 | 10.3 | A | A | A | A | A | — |
| Ex. 2 | — | 102 | 11.0 | A | A | A | A | A | — |
| Ex. 3 | — | 100 | 12.9 | A | A | A | A | A | — |
| Ex. 4 | — | 108 | 11.1 | A | A | A | A | A | — |
| Ex. 5 | — | 389 | 10.3 | A | A | A | A | A | — |
| Ex. 6 | — | 34 | 10.4 | A | A | A | A | A | — |
| Ex. 7 | — | 210 | 10.3 | A | A | A | A | A | — |
| Ex. 8 | Cupra filament non-woven fabric | 115 | 19.3 | A | — | — | A | A | A |
| Ex. 9 | — | 121 | 10.5 | A | A | A | A | A | — |

TABLE 1-continued

| | | | | | | | | | | |
|---|---|---|---|---|---|---|---|---|---|---|
| Ex. 10 | | 98 | 10.3 | B | B | B | A | A | — |
| Ex. 11 | | 117 | 10.4 | A | A | A | A | A | — |
| Comp. Ex. 1 | | 106 | 10.0 | C | C | C | — | — | — |
| Comp. Ex. 2 | | 108 | 11.0 | A | A | C | — | — | — |
| Comp. Ex. 3 | Cupra filament non-woven fabric | 120 | 19.0 | C | — | — | — | — | C |
| Comp. Ex. 4 | — | 87 | 11.0 | — | C | C | C | C | — |
| Comp. Ex 5 | — | 104 | 10.3 | C | C | C | Not observed | Not observed | — |

*[1] Mixture of 1-hexanol at 1.2% by weight and hydroxypropylmethyl cellulose at 0.012% by weight
*[2] Solid content weight percentage of Meikanate WEB per sample cellulose content following heat treatment Concenrtation in immersion bath is 2.1 percent by weight
*[3] PAS-H-10L, polydiallyl-dimethyl ammonium chloride The following measurements were carried out on the sheets of Examples 1 to 4 and Comparative Example 1. The results are shown in the following Table 2.

(1) Hydrophobicity Evaluation (Liquid Absorption Time)

4 µl of distilled water (20° C.) were dropped onto a fine cellulose fiber sheet followed by measuring the amount of time required for the liquid droplet to be absorbed. A longer amount of time for the droplet to be absorbed was judged to indicate greater hydrophobicity.

(2) Air Permeability Resistance

Humidity was adjusted in an atmosphere at a temperature of 20° C. and humidity of 50% RH. The humidity-adjusted sample was measured for air permeability resistance at 10 locations using an Oken type air permeability tester (Model EG01, Asahi Seiko Co., Ltd.), and the average value thereof was taken to be the air permeability resistance of that sample.

TABLE 2

| | Sample name | Liquid Absorption Time sec | Air Permeability Resistance sec/100 ml |
|---|---|---|---|
| Example 1 | S1 | 16 | 30,000 |
| Example 2 | S2 | 37 | 150,000 |
| Example 3 | S3 | 67 | 1,000,000 |
| Example 4 | S4 | 180 | 2,000 |
| Comparative Example 1 | R1 | 10 | 20,000 |

R1 not containing blocked polyisocyanate was most hydrophilic sheet. In contrast, when Meikanate WEB was added, liquid absorption time was determined to become longer and hydrophobicity was determined to increase as the added amount increased (S1-S3). However, in the case of S4 in which Meikanate CX was used, liquid absorption time was longer and hydrophobicity was determined to be greater than that at any concentration of Meikanate WEB.

In addition, when R1, which does not contain blocked polyisocyanate, is used for the reference, air permeability resistance increased as the added amount of Meikanate WEB increased in systems in which Meikanate WEB was added (S1-S3). On the other hand, air permeability resistance decreased in the case of S4, in which Meikanate CX is used.

The experimental conditions and results for Example 1 and Comparative Examples 6 and 7 are shown in the following Table 3.

Comparative Example 6

Needle bleached kraft pulp (NBKP) was dispersed in water to a concentration of 2.5% by weight to obtain an aqueous dispersion (400 L), and beating treatment was carried out for about 40 minutes on 400 L of the aqueous dispersion using the same Model SDR14 Lab Refiner (pressurized disk type) used in Example 1 for the disc refiner device at a clearance between disks of 0.8 mm to obtain a beaten slurry having a CSF value of 90 ml↓. Papermaking, drying and heat treatment were carried out in the same manner as Example 1 with the exception of adding 25.0 g of this slurry to 1.6 g of cationic blocked polyisocyanate ("Meikanate WEB", diluted to a solid content concentration of 1.0% by weight, 0.5% by weight based on weight of cellulose solid fraction) and 185.9 g of water to obtain R6.

Comparative Example 7

Diameter reduction, papermaking slurry preparation, papermaking, drying and heat treatment were carried out in the same manner as Comparative Example 6 with the exception of changing the amount of cationic blocked polyisocyanate added to 9.6 g (3% by weight based on weight of cellulose solid fraction) to obtain R7.

TABLE 3

| | | Fine Cellulose Fibers | | Blocked Polyisocyanate Aqueous Dispersion | | | Avg. Fiber Diameter nm | Basis Weight g/m² | Papermaking Ability | Wet Strength per 10 g of Basis Weight N/15 mm |
|---|---|---|---|---|---|---|---|---|---|---|
| | Sample Name | Type | Concentration (wt %) | Type | Concentration (wt %) | Addition Method | | | | |
| Example 1 | S1 | Linter pulp | 0.2 | Meikanate WEB | 3.0 | Internal | 110 | 10.3 | A | 1.32 |

TABLE 3-continued

| | Sample Name | Fine Cellulose Fibers Type | Concentration (wt %) | Blocked Polyisocyanate Aqueous Dispersion Type | Concentration (wt %) | Addition Method | Avg. Fiber Diameter nm | Basis Weight g/m² | Papermaking Ability | Wet Strength per 10 g of Basis Weight N/15 mm |
|---|---|---|---|---|---|---|---|---|---|---|
| Comp. Ex. 6 | R6 | NBKP | 1.0 | Meikanate WEB | 0.5 | Internal | 14,000 | 50.3 | C | 0.21 |
| Comp. Ex. 7 | R7 | NBKP | 1.0 | Meikanate WEB | 3.0 | Internal | 14,000 | 51.5 | C | 0.24 |

R6 and R7 having extremely large fiber diameters did not undergo a change in papermaking ability attributable to cationic blocked polyisocyanate. In the case of a sheet composed of fine cellulose fibers such as S1, the large specific surface area of the fine cellulose fibers is thought to have enabled them to be more effectively aggregated by the cationic blocked polyisocyanate. In addition, NBKP, having a large fiber diameter, has fewer interlacing points between fibers in comparison with fine cellulose fibers. Consequently, wet strength is thought to have become extremely weak in a sheet having low basis weight in which there are few interlacing points per unit area. In addition, due to the low specific surface area, the adsorbed amount of cationic blocked polyisocyanate becomes saturated at a lower added amount. Consequently, wet strength did not improve in R7 despite having increased the amount of cationic blocked polyisocyanate in comparison with R6. Thus, in the fabrication of a sheet having a low basis weight of, for example, 1 g/m² to 30 g/m² in particular, NBKP is unable to withstand substantial use from the viewpoint of wet strength. On the other hand, fine cellulose fibers enable the fabrication of a sheet having a low basis weight that is able to withstand substantial use from the viewpoint of wet strength.

The experimental conditions and results for Example 12 and Comparative Example 8 are shown in the following Table 4.

Example 12

After adding 1.9 g of cationic blocked polyisocyanate equivalent to 3% by weight based on the weight of the cellulose solid fraction and stirring for 3 minutes in the papermaking slurry production of Example 6, 6.3 g of a water repellent (trade name: "AG-E082", Asahi Glass Co., Ltd., diluted to solid content concentration of 1.0%) were dropped in at 10% by weight based on the weight of the cellulose solid fraction and stirred for 3 minutes to obtain a papermaking slurry. Papermaking, drying and heat treatment were carried out in the same manner as Example 6 using this papermaking slurry to obtain S12.

Comparative Example 8

Diameter reduction, papermaking slurry preparation, papermaking, drying and heat treatment were carried out in the same manner as Example 12 with the exception of not adding cationic blocked polyisocyanate to obtain R8.

(1) Pretreatment for Evaluating Water Repellent Immobilization

Pretreatment for evaluating the degree of immobilization of the water repellent was carried out by immersing 25 cm×25 cm sheets of S12 and R8 obtained in Example 12 and Comparative Example 8, respectively, in a glass vial containing 500 ml of butyl acetate followed by shaking for 1 day at a shaking speed of 200 rpm.

Subsequently, the sheets were dried in a vacuum at room temperature followed by evaluation of changes in moisture permeability, water bearing pressure and static contact angle.

(2) Change in Moisture Permeability

Moisture permeability of the samples before and after pretreatment was evaluated by measuring the moisture permeability per 24 hours (g/m²·24 h) in an environment at a temperature of 40° C. and humidity of 90% RH in accordance with method B-1 described in JIS L1099. A moisture permeability retention rate before and after pretreatment of 80% or more was evaluated as A, a retention rate of 50% or more was evaluated as B, and a retention rate of less than 50% was evaluated as C.

Retention rate (%)=moisture permeability after pretreatment/moisture permeability before pretreatment×100

(3) Change in Water Bearing Pressure

Water bearing pressure of the samples before and after pretreatment was evaluated by measuring in compliance with method B (high water pressure method) of the test method for water resistance of textiles of JIS L1092-1998. A water bearing pressure retention rate of 80% or more was evaluated as A, a retention rate of 50% or more was evaluated as B, and a retention rate of less than 50% was evaluated as C.

Retention rate (%)=water bearing pressure after pretreatment/water bearing pressure before pretreatment×100

(4) Change in Static Contact Angle

Static contact angle of the samples before and after pretreatment was evaluated by dropping 4 μl of distilled water (20° C.) onto a sheet and measuring the contact angle 1 second after the droplet contacts the sheet with an automated contact angle meter (trade name: "DM-301", Kyowa Interface Science Co., Ltd.). A static contact angle retention rate of 80% or more was evaluated as A, a retention rate of 50% or more was evaluated as B, and a retention rate of less than 50% was evaluated as C.

Retention rate (%)=static contact angle after pretreatment/static contact angle before pretreatment×100

TABLE 4

| | Sample Name | Fine Cellulose Fibers | | Blocked Polyisocyanate Aqueous Dispersion | | | Other Additives | | |
|---|---|---|---|---|---|---|---|---|---|
| | | Type | Concentration (wt %) | Type | Concentration (wt %) | Addition Method | Type | Concentration (wt %) | Addition Method |
| Example 12 | S12 | Manila hemp | 0.2 | Meikanate WEB | 3.0 | Internal | Water repellent*4 | 10 | Internal |
| Comp. Ex. 8 | R8 | Manila hemp | 0.2 | — | — | — | Water repellent*4 | 10 | Internal |

| | Base Material | Avg. Fiber Diameter nm | Basis Weight g/m$^2$ | Change in Moisture Permeability | Change in Water Bearing Pressure | Change in Contact Angle |
|---|---|---|---|---|---|---|
| Example 12 | — | 38 | 11.3 | A | A | A |
| Comp. Ex. 8 | — | 36 | 11.0 | C | C | C |

*4AsahiGuard AG-E082

In the case of S12, in which cationic blocked polyisocyanate was added, there was little change in moisture permeability, water bearing pressure or static contact angle even if immersed in butyl acetate. Namely, the water repellent is thought to not have undergone swelling or dissolution by butyl acetate. On the other hand, in the case of R8, in which cationic blocked polyisocyanate was not added, there were large changes in moisture permeability, water bearing pressure and static contact angle before and after immersion. This is thought to be the result of swelling and dissolution of the water repellent due to immersion in butyl acetate. On the basis of the above, the use of cationic blocked polyisocyanate was indicated to be effective for improving solvent resistance, for example, as a result of the water repellent being able to be immobilized on the fine cellulose fibers.

The experimental conditions and results of Examples 5, 13 and 14 and Comparative Example 9 are shown in the following Table 5.

Example 13

After adding 1.9 g of cationic blocked polyisocyanate equivalent to 3% by weight based on the weight of the cellulose solid fraction and stirring for 3 minutes in the papermaking slurry production of Example 5, an anionic polymer in the form of polystyrene sulfonate (trade name: "PS-50", Tosoh Corp., 6.3 g of solution diluted to a solid content concentration of 1.0% by weight) was added and stirred for 3 minutes. The remainder of the procedure was carried out in the same manner as Example 5 using this papermaking slurry to obtain S13.

Example 14

A cationic antimicrobial agent in the form of a copolymer of polydicyandiamide and polyalkylene polyamine (trade name: "Sensil 555", Senka Corp., 12.6 of solution diluted to solid content concentration of 1.0% by weight) was further added to the papermaking slurry produced in Example 13 followed by stirring for 3 minutes. The remainder of the procedure was carried out in the same manner as Example 13 to obtain S14.

Comparative Example 9

Diameter reduction, papermaking slurry preparation, papermaking, drying and heat treatment were carried out in the same manner as Example 5 with the exception of not adding cationic blocked polyisocyanate to obtain R9.

(1) Surface Zeta Potential

Zeta surface potential was measured by rinsing the samples with ultrapure water, placing the samples in a plate sample cell so that the surfaces of the fine cellulose fibers contacted a monitoring particle solution (polystyrene latex, pH 6.8), and measuring with an electrophoretic light scattering photometer (Zetasizer Nano ZS, Malvern instruments Ltd.).

(2) Pigment Removal Property 3 ml of an aqueous solution containing 1 ppm of an anionic pigment in the form of Orange II (Kanto Chemical Co., Ltd.) was completely filtered at a differential pressure of 100 kPa and effective filtration area of 3.5 cm$^2$ using the sample as a filtering material. The concentration C (ppm) of the filtrate was measured and anionic pigment removal rate (%) was calculated according to the equation indicated below.

$$\text{Anionic pigment removal rate (\%)} = (1-C) \times 100$$

The Orange II concentration C (ppm) of the filtrate can be measured by using an ultraviolet-visible spectrophotometer (V-650, Jasco Corp.) and preparing a calibration curve of known concentrations of Orange II (wavelength: 485 nm). In addition, the removal rate of a cationic pigment can be calculated using the same method as described above by using methylene blue (wavelength: 665 nm) instead of Orange II.

At this time, a removal rate of 80% or more was evaluated as A, a removal rate of 50% or more was evaluated as B, and a removal rate of less than 50% was evaluated as C.

(3) Evaluation of Antimicrobial Activity

Evaluation of antimicrobial activity was carried out in accordance with the antimicrobial fabric test (unified test method) enacted in JIS-1902-1998. More specifically, 2 g of sample were preliminarily placed in the bottom of a closed container, 0.2 ml of a microbial suspension of preliminarily cultured *Staphylococcus aureus* (test species: AATCC-6538P) diluted by a factor of 1/50 with broth was disseminated on the sample, and after allowing to stand undisturbed for 18 hours in an incubator at 37° C., 20 mL of SCDLP medium were added following by shaking well to rinse off the bacteria. The bacteria were then placed on ordinary agar medium and counted after 24 hours, and antimicrobial activity was evaluated by comparing with the bacterial count obtained from an unprocessed sample fabric treated in the same manner:

$$D=(Ma-Mb)-(Mc-Md)$$

wherein,

Ma: Log of viable bacteria count after culturing unprocessed sample for 18 hours;
(average of 3 specimens)
Mb: Log of viable bacteria count immediately after inoculating unprocessed sample;
(average of 3 specimens)
Mc: Log of viable bacterial count after culturing processed fabric for 18 hours;
Md: Log of viable bacteria count immediately after inoculating processed fabric; and
D: Viable bacteria activity value Bacterial activity was judged to have been demonstrated when the viable bacterial activity value was such that D≥2.2. The case of D≥2.2 was evaluated as A, while the case of D<2.2 was evaluated as C.

tion, antimicrobial activity, for example, was determined to be able to be imparted depending on the selection of the water-soluble polymer used.

Example 15

A mixed aqueous solution of calcium chloride and polyvinyl alcohol (trade name: "Gosenol EG-05", Nippon Synthetic Chemical Industry Co., Ltd.) (calcium chloride concentration: 20% by weight, polyviny alcohol concentration: 10% by weight) was uniformly coated onto S8 fabricated in Example 8 on the side of the cupra long fiber non-woven fabric using an applicator followed by drying in a drying oven to obtain S15.

Comparative Example 10

A mixed aqueous solution of calcium chloride and polyvinyl alcohol (trade name: "Gosenol EG-05", Nippon Synthetic Chemical Industry Co., Ltd.) (calcium chloride concentration: 20% by weight, polyvinyl alcohol concentration:

TABLE 5

| | Sample Name | Fine Cellulose Fibers | | Blocked Polyisocyanate Aqueous Dispersion | | | Other Additives | | |
|---|---|---|---|---|---|---|---|---|---|
| | | Type | Conc. (wt %) | Type | Conc. (wt %) | Addition Method | Type | Conc. (wt %) | Addition Method |
| Ex. 5 | S5 | Tencel | 0.2 | Meikanate WEB | 3.0 | Internal | — | — | — |
| Ex. 13 | S13 | Tencel | 0.2 | Meikanate WEB | 3.0 | Internal | Polyanion*4 | 10 | Internal |
| Ex. 14 | S14 | Tencel | 0.2 | Meikanate WEB | 3.0 | Internal | Polyanion*4/ Cationic antimicrobial agent*5 | 10/20 | Internal |
| Comp. Ex. 9 | R9 | Tencel | 0.2 | — | — | — | — | — | — |

| | Base Material | Avg. Fiber Diameter nm | Basis Weight g/m² | Zeta Potential mV | Anionic Pigment Adsorption | Cationic Pigment Adsorption | Antimicrobial Activity |
|---|---|---|---|---|---|---|---|
| Ex. 5 | — | 389 | 10.3 | 43 | A | C | C |
| Ex. 13 | — | 408 | 11.3 | −45 | C | A | C |
| Ex. 14 | — | 421 | 13.3 | 35 | A | C | A |
| Comp. Ex. 9 | — | 380 | 10.0 | −27 | Torn | Torn | Torn |

*4PS-50, polystyrene sulfonate
*5Sensil 555, polydicyandiamide-polyalkylene polyamine copolymer The zeta potential of S5 was cationic due to the effect of the cationic blocked polyisocyanate. Thus, although was able to adsorb anionic pigment, it was unable to remove cationic pigment. On the other hand, in the case of S13 that used a polyanion, the zeta potential became negative making it possible to remove cationic pigment. In addition, S14, in which a cationic antimicrobial agent was added to the slurry of S13 containing fine cellulose fibers having an anionic surface, demonstrated a cationic zeta potential in the same manner as S5 and demonstrated the ability to remove anionic pigment. In addition, the use of a cationic antimicrobial agent succeeded in imparting antimicrobial activity to the sheet. R9 demonstrated a negative zeta potential attributable to the fine cellulose fibers. However, in the cationic pigment removal test and antimicrobial activity test, the wet strength of the sheet was excessively weak resulting in difficulty in measurement. On the basis of the above, the use of this method was successful in controlling the zeta potential and adsorption performance of the sheets. In addi- 10% by weight) was uniformly coated onto R3 fabricated in Comparative Example 3 on the side of the cupra long fiber non-woven fabric using an applicator followed by drying in a drying oven to obtain R10.

(1) Moisture Permeability

Moisture permeability was evaluated by measuring the moisture permeability per 24 hours (g/m²·24 h) in an environment at a temperature of 40° C. and humidity of 90% RH in accordance with method A-1 described in JIS L1099.

(2) Film Thickness

A sample subjected to humidity adjustment in an atmosphere at a temperature of 20° C. and humidity of 50% RH was measured for thickness at 10 locations with the Automatic Micrometer manufactured by Hybridge Co., Ltd., and the average value thereof was taken to be the thickness of the sample.

(3) Air Permeability Resistance after Immersion

A sample was cut out to a size of 5 cm×5 cm, immersed in a plastic bottle containing 100 ml of distilled water, and shaken for 1 day at a shaking speed of 200 rpm. Following shaking, the sample was dried at room temperature and adjusted for humidity in an atmosphere at a temperature of 20° C. and humidity of 50% RH. Air permeability resistance of the humidity-adjusted sample was measured at 10 locations with an Oken type air permeability tester (Model EG01, Asahi Seiko Co., Ltd.), and the average value thereof was taken to be the air permeability resistance of the sample.

The experimental conditions and results for Example 15 and Comparative Example 10 are shown in the following Table 6.

TABLE 6

| | | Fine Cellulose Fibers | | Blocked Polyisocyanate Aqueous Dispersion | | | | Sample Before CaCl$_2$/PVA Coating | |
|---|---|---|---|---|---|---|---|---|---|
| | Sample Name | Type | Conc. (wt %) | Type | Conc. (wt %) | Addition Method | Base Material | Moisture permeability g/m$^2$ · 24 h | Air permeability resistance sec/100 ml |
| Ex. 15 | S15 | Linter pulp | 0.1 | Meikanate WEB | 3.0 | Internal | Cupra filament non-woven fabric | 7200 | 20000 |
| Comp. Ex. 10 | R10 | Linter pulp | 0.1 | — | — | — | Cupra filament non-woven fabric | 7300 | 12000 |

| | Sample After CaCl$_2$/PVA Coating | | | | | | | | |
|---|---|---|---|---|---|---|---|---|---|
| | CaCl$_2$ coated amount | PVA coated amount | Avg. fiber diameter | Basis weight | Thickness | Moisture permeability | Air permeability resistance | Air permeability resistance after immersion | Laminate Adhesion |
| Ex. 15 | 4.0 | 2.0 | 115 | 34.0 | 77 | 10000 | 890000 | 870000 | A |
| Comp. Ex. 10 | 4.0 | 2.0 | 120 | 35.1 | 76 | 9800 | 880000 | Unable to be measured*[6] | C |

*[6]The sheet structure of the fne cellulose fiber layer collapsed and was unable to be measured.

S15 was confirmed to demonstrate a dramatic improvement in air permeability resistance and moisture permeability as a result of coating S8 with calcium chloride and polyvinyl alcohol. These values satisfied the high levels of air permeability resistance and moisture permeability required by total heat exchanger sheets. In addition, as a result of immersing S15 in water and measuring air permeability resistance after drying, there was determined to be no change in air permeability resistance. This means that sheet structure of the fine cellulose fiber layer was maintained on the base material due to crosslinking by the blocked polyisocyanate. Moreover, as a result of the polyvinyl alcohol remaining in S15, a high level of air permeability resistance was confirmed to be retained. The above results indicated that the sheet demonstrates low gas permeability of the film even if moistened by water, and retained the "function of isolating gas even if moistened with water" as required by total heat exchanger sheets.

On the other hand, R10 was also confirmed to demonstrate a dramatic improvement in air permeability resistance and moisture permeability as a result of coating R3 with calcium chloride and polyvinyl alcohol. However, as a result of immersing in water, the sheet structure of the fine cellulose fiber layer collapsed and separation from the base material occurred. Thus, it lost the "function of isolating gas even if moistened with water" as required by total heat exchanger sheets.

Namely, the use of blocked polyisocyanate and polyvinyl alcohol was determined to be effective in terms of providing a total heat exchanger sheet.

INDUSTRIAL APPLICABILITY

The fine cellulose fiber sheet of the present invention is characterized by precisely controlling water resistance along with various properties and functions such as papermaking ability, solvent resistance, adhesion, functionalization agent immobilization, surface zeta potential, hydrophilicity/hydrophobicity or air permeability resistance. As a result, it can be deployed in a wide range of applications. For example, as a result of improving the water resistance of the fine cellulose fiber sheet with a blocked polyisocyanate, the sheet can be applied to water treatment membranes, separation membranes, cell culture sheets and total heat exchanger sheets used in an aqueous environment or highly wet environment. As a result of immobilizing a functionalization agent within and/or on the surface of a fine cellulose fiber layer with a blocked polyisocyanate, elution of the functionalization agent outside the sheet can be inhibited in applications in which the sheet contacts a liquid such as a liquid filter, and suppresses deterioration of performance when used for a long period of time. In a laminated structure consisting of a sheet composed of fine cellulose fibers and a sheet composed of an organic polymer, as a result of the fine cellulose fiber sheet and the organic polymer sheet being crosslinked and adhered by blocked polyisocyanate, the sheets are resistant to separation, thereby enabling the laminated structure to be used in water or in a highly wet environment. In addition, in the case of using as a filler of a fiber-reinforced plastic, as a result of being able to control hydrophilicity and hydrophobicity, the filler can be easily compounded with a desired polymer.

The invention claimed is:
1. A laminated structure in which a fine cellulose fiber sheet that fulfills all of the following requirements (1)-(6):
   (1) it comprises fine cellulose fibers having an average fiber diameter of 2 nm to 1000 nm and a blocked polyisocyanate;
   (2) the weight ratio of the fine cellulose fibers is 50% by weight to 99% by weight;
   (3) the blocked polyisocyanate aggregate is uniformly distributed in the sheet in the planar direction and thickness direction:
   (4) the weight ratio of the blocked polyisocyanate aggregate to the fine cellulose fibers is 1% by weight to 100% by weight;
   (5) the blocked polyisocyanate aggregate is chemically bound to the fine cellulose fibers; and
   (6) wet/dry strength ratio is 70% or more, and a sheet composed of an organic polymer are laminated, wherein the fine cellulose fiber sheet and the sheet composed of an organic polymer are chemically cross-linked by the blocked polyisocyanate aggregate.
2. The laminated structure according to claim 1, wherein a hydrophilic compound is contained in the laminated structure at 1% by weight to 50% by weight as the weight ratio of the laminate.
3. The laminated structure according to claim 2, wherein the hydrophilic compound contains at least one type of compound selected from inorganic salts consisting of lithium chloride, calcium chloride and magnesium chloride, carboxymethyl cellulose, carboxyethyl cellulose, hydroxyalkyl cellulose and salts or crosslinked products thereof, and organic compounds consisting of polyethylene glycol, polypropylene glycol and polyvinyl alcohol.
4. A method for producing the laminated structure according to claim 1, comprising the following steps:
   a preparation step for preparing an aqueous dispersion comprising fine cellulose fibers and a water-dispersible blocked polyisocyanate,
   a papermaking step for dehydrating the aqueous dispersion on a sheet composed of an organic polymer by filtration and forming a moisture-containing laminated structure in which a fine cellulose fiber layer is laminated on a sheet composed of the organic polymer,
   a step for drying the moisture-containing laminated structure, and
   a heating step for heating the dried laminated structure.
5. A water treatment membrane comprising the laminated structure according to claim 1.
6. A separation membrane comprising the laminated structure according to claim 1.
7. A cell culture sheet comprising the laminated structure according to claim 1.
8. A structure composed of a fiber-reinforced plastic comprising the laminated structure according to claim 1.
9. A total heat exchanger sheet comprising the laminated structure according to any of claims 1 to 3.
10. The total heat exchanger sheet according to claim 9, wherein the average thickness of the laminated structure is 10 μm to 100 μm.
11. A total heat exchange element in which the total heat exchanger sheet according to claim 9 is used as a partition that divides two types of air flow having different temperature, different humidity or both.
12. A total heat exchanger that comprises the total heat exchange element according to claim 11.
13. The laminated structure according to claim 1, wherein the blocked polyisocyanate aggregate has a cationic group.
14. The laminated structure according to claim 1, wherein at least one type of functionalization agent selected from the group consisting of a water-repellent oil processing agent, water-soluble polymer, antimicrobial polymer, thermoplastic resin, thermosetting resin and photocurable resin is immobilized inside and/or on a surface of the fine cellulose fiber sheet by the blocked polyisocyanate aggregate.
15. A structure composed of a fiber-reinforced plastic comprising a fine cellulose fiber sheet that fulfills all of the following requirements (1) to (6):
   (1) it comprises fine cellulose fibers having an average fiber diameter of 2 nm to 1000 nm and a blocked polyisocyanate aggregate;
   (2) the weight ratio of the fine cellulose fibers is 50% by weight to 99% by weight;
   (3) the blocked polyisocyanate aggregate is uniformly distributed in the sheet in the planar direction and thickness direction;
   (4) the weight ratio of the blocked polyisocyanate aggregate to the fine cellulose fibers is 1% by weight to 100% by weight;
   (5) the blocked polyisocyanate aggregate is chemically bound to the fine cellulose fibers; and
   (6) wet/dry strength ratio is 70% or more.
16. A total heat exchanger sheet comprising a fine cellulose fiber sheet that fulfills all of the following requirements (1) to (6):
   (1) it comprises fine cellulose fibers having an average fiber diameter of 2 nm to 1000 nm and a blocked polyisocyanate aggregate;
   (2) the weight ratio of the fine cellulose fibers is 50% by weight to 99% by weight;
   (3) the blocked polyisocyanate aggregate is uniformly distributed in the sheet in the planar direction and thickness direction;
   (4) the weight ratio of the blocked polyisocyanate aggregate to the fine cellulose fibers is 1% by weight to 100% by weight;
   (5) the blocked polyisocyanate aggregate is chemically bound to the fine cellulose fibers; and
   (6) wet/dry strength ratio is 70% or more.
17. The total heat exchanger sheet according to claim 16, wherein the average thickness of the laminated structure is 10 μm to 100 μm.
18. A total heat exchange element in which the total heat exchanger sheet according to claim 16 is used as a partition that divides two types of air flow having different temperature, different humidity or both.
19. A total heat exchanger that comprises the total heat exchange element according to claim 18.

* * * * *